United States Patent [19]

Studt et al.

[11] Patent Number: 4,486,439

[45] Date of Patent: Dec. 4, 1984

[54] TREATMENT OF COCCIDIOSIS

[75] Inventors: William L. Studt, Harleysville; Donald E. Kuhla, Doylestown; Billy J. Chou, Paoli; John Yelnosky, Warrington, all of Pa.

[73] Assignee: William H. Rorer, Inc., Fort Washington, Pa.

[21] Appl. No.: 451,168

[22] PCT Filed: Aug. 24, 1981

[86] PCT No.: PCT/US81/01142

§ 371 Date: Sep. 16, 1982

§ 102(e) Date: Sep. 16, 1982

[87] PCT Pub. No.: WO83/00625

PCT Pub. Date: Mar. 3, 1983

[51] Int. Cl.$^3$ .................. A61K 31/44; A61K 31/17

[52] U.S. Cl. ..................... 424/263; 424/244; 424/246; 424/248; 424/250; 424/251; 424/258; 424/269; 424/270; 424/272; 424/273 P; 424/275; 424/285; 424/304; 424/322; 424/248.54

[58] Field of Search ............... 424/322, 274, 285, 275, 424/273, 272, 270, 269, 263, 251, 258, 304, 244, 248, 250, 246

[56] References Cited

PUBLICATIONS

Goodford et al., Brit. J. Pharmacol. vol. 48 (1973) pp. 650–654.

Primary Examiner—Sam Rosen
Attorney, Agent, or Firm—James A. Nicholson; Alexis Barron; Martin F. Savitzky

[57] ABSTRACT

A method for the preventive and curative treatment of coccidial infections in humans and other animals comprising the administration thereto of an amidinourea of amidinothiourea.

41 Claims, No Drawings

TREATMENT OF COCCIDIOSIS

FIELD OF THE INVENTION

This invention relates to the health management of animal populations and to a method for the prophylactic and curative treatment of parasitic protozoal infections in animals, including mammalian and avian species. This invention also relates to the suppression of a particular parasitic class of Protozoa, namely Sporozoa, species of which commonly infect the gastrointestinal tract, renal tubules, cecum and liver of animals and, in particular, animals of the avian species.

All members species of the Sporozoan class of Protozoa are parasitic. A particular subdivision of Sporozoa, namely, Coccidia, is of particular interest. This subdivision, includes the genera, Eimeria, Isospora, Klossiella and Hepatozoon, which are responsible for the disease condition known as coccidiosis.

Coccidia species infect chickens, canines, felines, rabbits, cattle, sheep and goats, swine, geese, mice, rats, frogs, guinea pigs and man, among others. Coccidosis affects the living host adversely in many ways depending upon the tissue preference of the particular parasite involved and the number of oöcysts in the initial infection. There are as many kinds of coccidiosis as there are species of coccidia, each with its characteristic signs. In many cases, infection may result in the death of the host animal.

Coccidiosis is a disease which starts with the oöcyst, the egg-like form of the parasite. Under favorable conditions, oöcysts sporulate and become infective. Infection can be readily spread throughout an entire population of animals, such as, sheep and cattle in a feed lot or pasture, chickens in pens, and, canines and felines, through the release of coccidia oöcysts in fecal waste, followed by oöcyst ingestion by uninfected animals.

As a group, the coccidioses of chickens cause more severe financial loss than is encountered in other domesticated avian species. Losses following a severe outbreak may be devastating. Turkeys, geese, ducks and guinea fowl suffer less severely from intestinal coccidiosis infection than do chickens; however, economic losses occur under certain conditions in all these birds.

In spite of recent advances in the prevention and control of coccidiosis through chemotherapy, the disease remains a major problem in the poultry industry. Unlike many other poultry diseases, coccidia are almost universally found wherever chickens are being raised.

The resistant oöcysts are readily transported in live birds which sometime remain carriers for long periods of time. Because most coccidial infections are subclinical, the poultry producer is usually unaware of the presence of several species of organisms infecting his flock until mismanagement permits an explosive development of a large number of sporulated oöcysts.

Of the four genera of Sporozoa mentioned above, the genus Eimeria includes the species of coccidia responsible for coccidiosis in chickens. The nine recognized species of Eimeria reported in chickens are: *Eimeria acervulina; Eimeria brunetti; Eimeria hagani; Eimeria maxima; Eimeria mivati; Eimeria mitis; Eimeria necatrix; Eimeria praecox;* and *Eimeria tenella.* The differential pathological characteristics of infections caused by these species of coccidia are discussed in the article by W. Malcolm Reid, entitled, "Coccidiosis", in *Diseases of Poultry,* Sixth Edition, Iowa State U. Press (1972).

REPORTED DEVELOPMENTS

The sulfa drugs were first used to suppress coccidiosis in poultry, but of these drugs only a few are currently being used. Their major disadvantage is that administration of high levels of the drug for extended periods of time may result in the development of hemorrhagic syndrome.

Anticoccidal formulations currently used in feed compositions include: sulfaquinoxaline; nitrofurazone; nitrophenide; sulfanitran; arsenobenzene; a mixture of butynorate, sulfanitran, dinsed, and roxarsone; nicarbazin; a mixture of nitrofurazone, furazolidone, bithionol, and methiotriazamine; a mixture of 2,4-diamino-5-(p-chlorophenyl)-6-ethyl-pyrimidine and sulfaquinoxaline; furazolidine; glycarbylamide; a mixture of nitromide, sulfanitran, and roxarsone; oxytetracycline; amprolium; chlortetracycline; zoalene; a mixture of amprolium and ethopabate; nihydrazone; a mixture of aklomide and sulfanitran; buquinolate; clopidol; decoquinate; and monensin.

Toxicity is a serious drawback to the use of many of the currently available anti-coccidials, such as, monensin. A variation in dose of as little as 20% can be detrimental, if not fatal, to medicated poultry while a decrease in dose of 20% may result in an ineffective therapy. Furthermore, a major problem with anti-coccidial drugs is that the coccidia species may develop drug resistance under conditions of low-level prophylactic use of the anticoccidial compound. Additionally, government regulations relating to acceptable levels of drug residues in animal tissue destined for human consumption require the withdrawal of the anticoccidial agent in the animals' feed weeks prior to their going to market. Hence, the risk of an outbreak of coccidiosis just prior to slaughter is great.

This invention relates to the discovery that a relatively non-toxic class of ureas and thioureas exhibits surprisingly effective activity against parasitic sporazoa, and, in particular, is useful in the treatment of coccidiosis.

SUMMARY OF THE INVENTION

This invention relates to a method for the suppression of coccidial infections in animals comprising administering to an animal exposed to Coccidia an effective amount of an amidinourea or amidinothiourea.

Representative compounds found useful in the prophylactic or curative treatment of coccidiosis in populations of animals including infected members comprise an anti-coccidial compound according to Formula I or Formula II

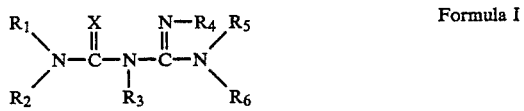

Formula I

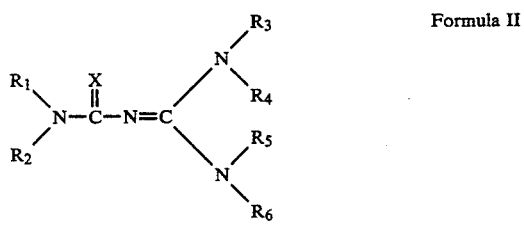

Formula II wherein:

X is oxygen or sulfur;

$R_1$, $R_2$, $R_3$, $R_4$, $R_5$ and $R_6$ are hydrogen, alkyl, cycloalkyl, cycloalkenyl, bicycloalkyl, alkenyl, alkynyl, alkoxy, hydroxy, haloalkyl, haloalkenyl, hydroxyalkyl, alkoxyalkyl, cyanoalkyl, aminoalkyl, mono- or di- alkyl aminoalkyl, carbamoylalkyl, mono- or di- alkyl carbamoyl lower alkyl, alkoxy carbamoylalkyl, aralkoxy carbamoylalkyl, acyl, alkylsulfonyl, aralkylsulfonyl, aryl, aralkyl, heterocyclyl, substituted heterocyclyl, heterocyclylalkyl, or substituted heterocyclylalkyl;

$R_1$ and $R_2$ together with the nitrogen to which they are attached may form a mono- or bicyclic 5 to 10 member heterocycle containing 0 to 4 additional heteroatoms of oxygen, nitrogen or sulfur;

$R_5$ and $R_6$ together with the nitrogen to which they are attached may form a mono- or bicyclic 5 to 10 member heterocycle, containing 0 to 4 additional heteroatoms of oxygen, nitrogen or sulfur;

$R_4$ and $R_5$ together with the nitrogens to which they are attached may form a mono- or bicyclic 5 to 10 member heterocycle, containing 0 to 4 additional heteroatoms of oxygen, nitrogen or sulfur;

provided that at least one of $R_1$, $R_2$, $R_3$, $R_4$, $R_5$ and $R_6$ is other than hydrogen;

and, pharmaceutically acceptable salts thereof.

The present invention can be used to particular advantage in the treatment of coccidiosis in avian species, for example, poultry, and encompasses a method of prophylactic and curative therapy using a pharmaceutical composition, feed mixture or liquid supplement containing one or more amidinoureas or amidinothioureas, including those within the scope of Formulae I and II above.

This invention also relates to pharmaceutical preparations, and feed and liquid compositions, for prophylactic and curative treatment of coccidiosis utilizing amidinoureas and amidinothioureas.

DETAILED DESCRIPTION OF THE INVENTION

Amidinoureas and amidinothioureas include one of the isomeric structural groups

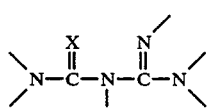

or

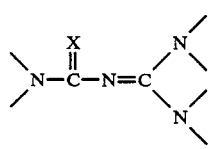

wherein X is oxygen or sulfur. In any discussion of the true structure of an amidinourea or amidinothiourea, tautomerism must be considered. (For convenience, the term "amidinourea" is hereafter used to encompass amidinothioureas). Those skilled in the art know that the amidinourea chain can be legitimately represented in any one of several tautomeric forms. When the amidinourea is in solution, one form may predominate over another depending upon the degree and location of substitution and on the nature of the solvent. The rates of conversion of one tautomer to another will depend upon the nature of the solvent, the degree of hydrogen bonding permitted, the temperature, and possibly other factors (such as pH, trace impurities and the like).

To illustrate what is meant by this, a number of likely structures are here shown for two of the compounds of this invention:

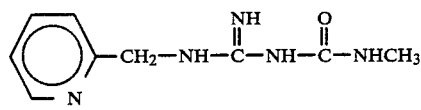

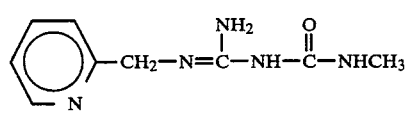

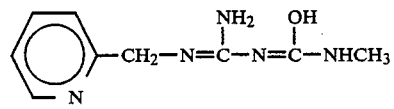

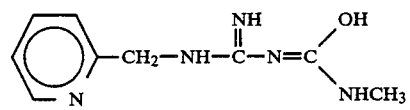

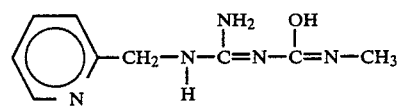

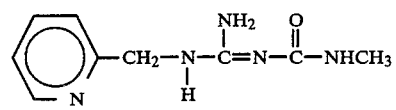

Other structures are also possible, such as those with hydrogen bonding.

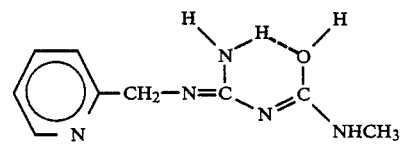

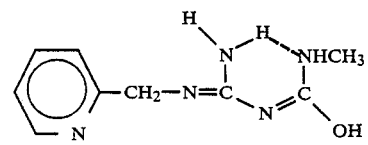

Furthermore, the heterocyclic atom may contribute to structures reflecting hydrogen bonding.

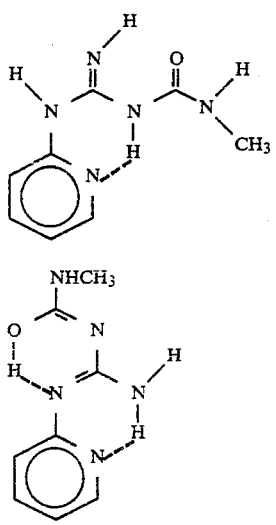

As employed above and throughout the disclosure, the following terms, unless otherwise indicated, shall be understood to have the following meanings:

"Alkyl" means a saturated aliphatic hydrocarbon which may be either straight- or branched-chain. Preferred groups have no more than about 12 carbon atoms and may be methyl, ethyl and structural isomers of propyl, butyl, pentyl, hexyl, heptyl, octyl, nonyl, decyl, undecyl and dodecyl.

"Lower alkyl" means an alkyl group as above, having 1 to 6 carbon atoms. Suitable lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group having 3 to 6 carbon atoms. Preferred groups are cyclopropyl, cyclopentyl and cyclohexyl.

"Alkenyl" means an unsaturated aliphatic hydrocarbon. Preferred groups have no more than about 12 carbon atoms and 1 to 3 carbon double bonds and may include straight or branched chains, and may be any structural and geometric isomers of ethenyl, propylenyl, butenyl, pentenyl, hexenyl, heptenyl, octenyl, nonenyl, decenyl, undecenyl, and dodecenyl or butadienyl, pentadienyl etc. Also included are the cycloalkylene groups such as cyclopropenyl, cyclopentenyl, cyclohexenyl, etc. and the cycloalkylalkylene groups such as cyclo-propylenelymethyl, and cyclohexenylmethyl and the like.

"Lower alkenyl" means alkenyl of 2 to 6 carbon atoms such ethylene, propylene, butylene, isobutylene, etc., including all structural and geometrical isomers thereof.

"Alkynyl" means an unsaturated aliphatic hydrocarbon. Preferred groups have no more than about 12 carbon atoms and contain one or more triple bonds, including any structural or geometric isomers of acetylenyl, propynyl, butynyl, pentynyl, hexynyl, heptynyl, octynyl, nonynyl, decynyl, undecynyl, dodecynyl, etc.

"Lower alkynyl" means alkynyl of 2 to 6 carbon atoms such as structural and geometric isomers of propargyl, butynyl, pentynyl, etc.

"Aryl" means a substituted or unsubstituted benzenoid aromatic or a bicyclic aromatic group including phenyl and substituted phenyl.

"Substituted phenyl" or a "substituted benzenoid aromatic or bicyclic aromatic" means a group in which one or more of the hydrogens has been replaced by the same or different substituents including halo, lower alkyl, halo-lower alkyl, nitro, amino, acylamino, hydroxyl, lower alkoxy, aryl lower alkoxy, acyloxy, cyano, halo-lower alkoxy or lower alkyl sulfonyl. The preferred substituted phenyl group is phenyl in which the 2 and 6 positions are substituted.

"Aralkyl" means an alkyl (preferably a lower alkyl) in which one or more hydrogens is substituted by an aryl moiety (preferably phenyl or substituted phenyl), e.g., benzyl, phenethyl, etc.

"Heterocyclyl" or "heterocycle" means a 3, 5, 6, 7, 8, 9 or 10 member ring having 1 to 5 hetero atoms which may be nitrogen, oxygen or sulfur, including, among others, pyridyl, pyrimidyl, pyrazolyl, imidazolyl, furyl, thienyl, oxazolyl, thiazolyl, piperidyl, morpholinyl, oxazolidinyl, thiazolidinyl, pyrazolodinyl, imidazolidinyl, piperazinyl, thiamorpholinyl, trimethylenetriaminyl and ethyleneiminyl; where the heterocycle may be mono-, di-, tri- or tetra- substituted by lower alkyl, lower alkenyl, lower alkynyl, aryl, aralkyl, halo, nitro, cyano, sulfonyl, hydroxyl, carboxyl, lower alkanoyl, lower carboalkoxy, lower alkoxy, aryl lower alkoxy, halo lower alkoxy, amido, amino, lower alkylamino, dialkylamino, lower alkoxyamino, and aralkylamino.

"Substituted heterocyclyl" means a heterocycle in which one or more of the hydrogens on the ring carbons have been replaced by substituents as given above with respect to substituted phenyl.

The terms "halo" and "halogen" include all four halogens; namely, fluorine, chlorine, bromine and iodine. The halo alkyls, halophenyl and halo-substituted pyridyl include groups having one or more halosubstituents which may be the same or different such as trifluoromethyl, 1-chloro-2-bromo-ethyl, chlorophenyl, 4-chloropyridyl, etc.

"Acyloxy" means an organic acid radical of a lower alkanoic acid or aromatic acid such as acetoxy, propionoxy, benzoyloxy, and the like.

"Acyl" means an organic radical of the formula RCO where R is alkyl or aromatic, such as, lower alkanoyl and aroyl. Exemplary acyl groups are acetyl, benzoyl, napthoyl, etc.

"Lower alkanoyl" means the acyl radical of a lower alkanoic acid such as acetyl, propionyl, butyryl, valeryl, stearoyl, and the like.

"Alkoxy" is intended to include hydroxy alkyl groups, preferably lower alkyl groups such as methoxy, ethoxy, n-propoxy, i-propoxy, and the like.

The preferred "aralkyl" groups are benzyl and phenethyl.

The preferred "halo lower alkyl" group is trifluoromethyl.

The preferred "halo lower alkoxy" group is trifluoromethoxy.

Among the amidinoureas or thioureas according to Formulae I and II, a preferred group of compounds suitable for use in the practice of this invention are compounds in which at least one of the $R_1$ and $R_5$ substituents is aryl, aralkyl, heterocyclyl, heterocyclylalkyl, substituted heterocyclyl or substituted heterocyclylalkyl.

A preferred subclass of amidinourea compounds according to Formulae I or II includes those wherein $R_1$ or $R_5$ is aryl or aralkyl.

A particularly preferred subclass of these compounds is represented by Formulae III and IV below:

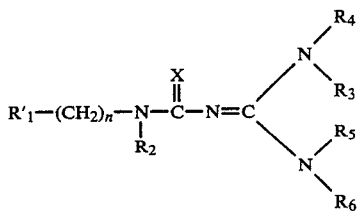

wherein:
X is oxygen or sulfur;
n is 0, 1, 2 or 3;
R'$_1$ is phenyl, substituted phenyl, heterocyclyl or heterocyclyl having one or more of the ring hydrogens replaced by lower alkyl, lower alkoxy, halo, halo lower alkyl, amino, acylamino, acyloxy, aryl lower alkoxy, halo lower alkoxy, nitro, hydroxy, cyano, carboxyl or lower alkyl sulfonyl;
and R$_2$, R$_3$, R$_4$, R$_5$ and R$_6$ are hydrogen, lower alkyl, lower alkoxy, lower alkenyl, cycloloweralkenyl, hydroxy, cycloloweralkyl, aryl, arloweralkyl, heterocyclyl, heterocyclyl lower alkyl, lower alkynyl, halo alkyl, hydroxy lower alkyl, lower alkoxy lower alkyl, cyano lower alkyl, amino lower alkyl, mono- or di- lower alkyl amino lower alkyl, carbamoyl lower alkyl, mono- or di- alkyl carbamoyl lower alkyl, lower alkoxy carbamoyl lower alkyl, aralkoxy carbamoyl lower alkyl, lower alkylacyl, alkyl sulfonyl or aralkyl sulfonyl; or
R$_5$ together with R$_6$ and the nitrogen to which R$_5$ and R$_6$ are attached or R$_5$ together with R$_3$ and the nitrogens to which they are attached may form a 5, 6, 7 or 8 membered heterocyclic ring which may include 0 to 2 additional hetero atoms which may be either oxygen, nitrogen or sulfur;
and pharmaceutically acceptable salts thereof;

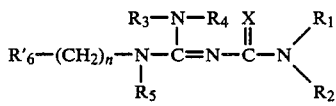

wherein:
X is oxygen or sulfur;
n is 0, 1, 2 or 3;
R'$_6$ is phenyl, substituted phenyl, heterocyclyl or heterocyclyl having one or more of the ring hydrogens replaced by lower alkyl, lower alkoxy, halo, halo lower alkyl, amino, acylamino, acyloxy, aryl lower alkoxy, halo lower alkoxy, nitro, hydroxy, cyano, carboxyl or lower alkyl sulfonyl;
and R$_1$, R$_2$, R$_3$, R$_4$ and R$_5$ are hydrogen; lower alkyl, lower alkoxy, lower alkenyl, cyclo lower alkenyl, hydroxy, cycloloweralkyl, aryl, arloweralkyl, heterocyclyl, heterocyclyl lower alkyl, lower alkynyl, halo alkyl, hydroxy lower alkyl, lower alkoxy lower alkyl, cyano lower alkyl, amino lower alkyl, mono- or di- lower alkyl amino lower alkyl, carbamoyl lower alkyl, mino- or di- alkyl carbamoyl lower alkyl, lower alkoxy carbamoyl lower alkyl, aralkoxy carbamoyl lower alkyl, lower alkylacyl, alkyl sulfonyl or aralkyl sulfonyl; or, R$_1$ together with R$_2$ and the nitrogen to which they are attached or R$_3$ together with R$_4$ and the nitrogen to which they are attached or R$_3$ together with R$_5$ and the nitrogen atoms to which they are attached, may form a 5, 6, 7 or 8 membered heterocyclic ring which may include 0 to 2 additional hetero atoms which may be either oxygen, nitrogen or sulfur;
and pharmaceutically acceptable salts thereof.

Preferred compounds within this subclass of amidinoureas include those according to Formulae V and VI.

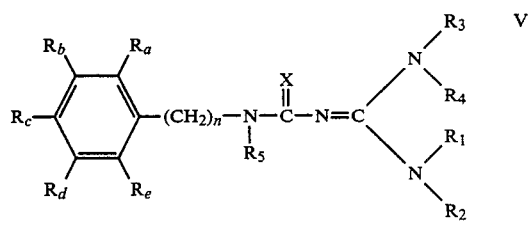

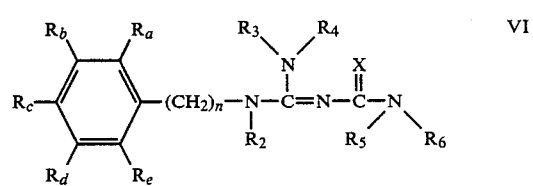

wherein:
n is 0, 1, 2 or 3;
R$_a$, R$_b$, R$_c$, R$_d$ and R$_e$ are selected from the group including hydrogen, halo, alkyl, alkenyl, cycloalkenyl, cycloalkyl, alkoxy, hydroxy, cyano, amino, acyl, nitro, acyloxy, haloalkyl, alkoxyalkyl, aminoalkyl, arylalkoxy, haloalkoxy, alkylsulfonyl and acylamino;
and, X, R$_1$, R$_2$, R$_3$, R$_4$, R$_5$ and R$_6$ are as defined above.

A further class of preferred amidinoureas useful in the practice of this invention includes compounds according to Formulae I and II wherein one of the R$_1$ or R$_5$ substituents is an ortho-substituted phenyl group.

A preferred series of compounds within this subclass are described according to Formulae VII and VIII.

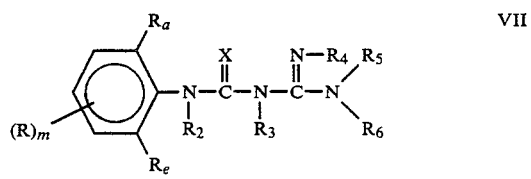

wherein:
X is oxygen or sulfur;
m is 0, 1, 2 or 3;
R, R$_a$, and R$_e$ are hydrogen, lower alkyl, halo, cyano, lower alkoxy, nitro, amino or halo lower alkyl;
R$_2$, R$_3$, R$_4$ and R$_5$ are hydrogen, lower alkyl, lower alkoxy, or halo lower alkyl;
R$_6$ is lower alkyl, lower alkoxy, halo lower alkyl, heterocyclyl or heterocyclyloweralkyl;
provided that at least one of R$_a$ or R$_e$ is other than hydrogen;
and pharmaceutically acceptable salts thereof.

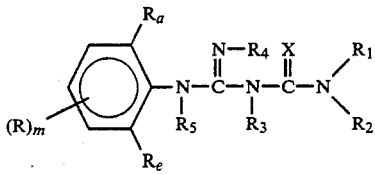

wherein:
X is oxygen or sulfur;
m is 0, 1, 2 or 3;
R, $R_a$ and $R_e$ are hydrogen, lower alkyl, halo, cyano, lower alkoxy, nitro, amino or halo lower alkyl;
$R_1$, $R_3$, $R_4$ and $R_5$ are hydrogen, lower alkyl, lower alkoxy, or halo lower alkyl;
$R_2$ is lower alkyl, lower alkoxy, halo lower alkyl, heterocyclyl or heterocyclyl lower alkyl;
provided that at least one of $R_a$ or $R_e$ is other than hydrogen;
and pharmaceutically acceptable salts thereof.

Another preferred subclass of amidinoureas and thioureas for use in the present invention includes compounds according to Formulae I or II, wherein at least one of $R_1$ and $R_5$ is heterocyclyl, heterocyclylalkyl, substituted heterocyclyl or substituted heterocyclylalkyl.

Exemplary heterocyclyl groups include 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 2-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole; where said heterocycle may be mono-, di-, tri- or tetra-substituted by ring substituents, such as, hydrogen, lower alkyl, lower alkenyl, aryl, lower alkynyl, aralkyl, halo, nitro, cyano, sulfonyl, hydroxyl, carboxyl, lower alkanoyl, lower alkoxy, aryl lower alkoxy, halo lower alkoxy, amido, amino, lower alkylacyloxy, alkylamino, lower alkoxyamino, and aralkoxyamino.

Particularly preferred compounds according to Formulae I to IV are those compounds wherein at least one of $R_1$ and $R_5$ is pyridyl, substituted pyridyl, pyridylalkyl or substituted pyridylalkyl, thiophenyl or substituted thiophenyl, thiophenylalkyl or substituted thiophenylalkyl, pyrrole or substituted pyrrole, pyrrolealkyl or substituted pyrrolealkyl; and the N- or S-oxides thereof. In the substituted heterocyclyl groups, the preferred positions of substitution are the positions vicinal to the heterocyclyl attachment to the amidinourea or thiourea chain.

A subdivision of the various subclasses of compounds defined above which are useful in the practice of this invention are compounds wherein $R_3$ is hydrogen. The presence of hydrogen in the $R_3$ position permits extensive tautomerism throughout the amidinourea chain.

Suitable amidinoureas for use as anti-coccidial agents are also disclosed: in *Arzneimittel Forschung*, 28(II), 1433–1480 (1978); in U.S. Pat. Nos.: 4,115,647; 4,088,785; 4,025,652; 4,115,564; 4,060,635; 4,246,409; 4,058,557 and 4,147,804; and in copending U.S. patent applications, each assigned to the assignee of the present application, Ser. Nos. 262,808, 262,811, and 140,135, filed in the United States as a PCT application on the same day (Aug. 24, 1981) as the present application, the disclosures of which are incorporated herein by reference. The aforementioned pending applications and other publications also disclose methods for preparing amidinoureas.

The nomenclature used for compounds useful in the practice of this invention is as follows.

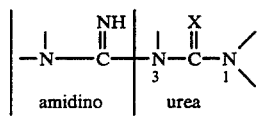

The urea nitrogens are designated as positions 1 and 3. It should be understood that alternate nomenclature can be used to adequately describe the compounds of this invention, one such system of nomenclature being based on the quanidine structure,

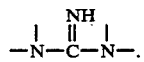

Representative examples of compounds useful in this invention are listed below in Tables I, I-A and 2.

TABLE I 1-(2-bromo,6-methylphenyl)-3-n-propylamidinourea
1-(2-chloro,6-methylphenyl)-3-ethylamidinourea
1-(2-chlorophenyl)-3-ethylamidinourea
1-(2,6-dimethylphenyl)-3-[(2-pyridylmethyl)amidino]urea
1-(2-chloro-6-methylphenyl)-3-[(2',2',2'-trifluoroethyl)-amidino]urea
1-(2,6-dimethylphenyl)-3-methylamidinourea
1-(2,6-dimethylphenyl)-3-(3-methylbutoxy)amidinourea
1-(2,6-dimethylphenyl)-3-n-propylamidinourea
O—chlorophenylamidinourea
(2,3-dichlorophenylamidino)urea
(2,4-dichlorophenylamidino)urea
(2,5-dichlorophenylamidino)urea
1-(2,6-dimethylphenyl)-3-(1',1',3',3'-tetramethylamidino)-urea
1-(2-bromo-6-methylphenyl)-3-(1',1',3',3'-tetramethyl-amidino)urea
(3,4-dichlorophenylamidino)urea
(3,5-dichlorophenylamidino)urea
(2,6-dichlorophenylamidino)urea
m-chlorophenylamidinourea
p-chlorophenylamidinourea
3,4-difluorophenylamidinourea
m-bromophenylamidinourea
p-bromophenylamidinourea
3,4-dibromophenylamidinourea
3-chloro-4-bromophenylamidinourea
3-bromo-4-chlorophenylamidinourea
3-chloro-4-fluorophenylamidinourea
3-bromo-4-fluorophenylamidinourea
3-fluoro-4-chlorophenylamidinourea
2,6-dimethylphenylamidinourea
2,6-diethylphenylamidinourea
2-methyl-6-ethylphenylamidinourea
2-methyl-6-methoxyphenylamidinourea
2-methyl-6-ethoxyphenylamidinourea
2-ethyl-6-ethoxyphenylamidinourea
3,4-dimethoxyphenylamidinourea
3,4-dihydroxyphenylamidinourea
3,4,5-trimethoxyphenylamidinourea
3,4,5-trihydroxyphenylamidinourea
1-(2,6-dimethylphenylamidino)-3,3-(N—methyl-3'-azapentamethylene)urea
1-(2,6-dimethylphenylamidino)-3,3-(N—methyl-3'-azahexa-

TABLE I-continued methylene)urea
1-(2,6-dimethylphenylamidino)-3,3-(3'-oxapentamethylene)urea
1-(2,6-dimethylphenylamidino)-3,3-(2,'-thiatetramethylene)urea
1-(2,6-dimethylphenylamidino)-3,3-tetramethyleneurea
1-(p-fluorophenylamidino)-3,3-(α,α '-dimethylpentamethylene)urea
1-(2,6-dimethylphenylamidino)-3,3'-(α,α'-dimethylpentamethylene)urea
1-(2,6-dimethylphenylamidino)-3,3-(pentamethylene)urea
1-(2,6-dimethylphenylamidino)-3,3-(α-methylpentamethylene)urea
1-(N—methylamidino)-3-(2,6-dimethylphenyl)urea
1-(N—methylamidino)-3-(2,6-diethylphenyl)urea
1-amidino-3-(2-methyl-6-chlorophenyl)urea
1-amidino-3-(2-methyl-6-bromophenyl)urea
1-amidino-3-(2-methyl-6-methoxyphenyl)urea
1-amidino-3-(2,6-dimethylphenyl)urea
1-amidino-3-(2-methyl-6-ethylphenyl)urea
1-amidino-3-(2-ethyl-6-chlorophenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-amidino-3-(2-methyl-6-chlorophenyl)urea
1-amidino-3-(2-methyl-6-bromophenyl)urea
1-amidino-3-(2,6-dimethyl-4-hydroxyphenyl)urea
1-amidino-3-(2,6-dimethyl-3-hydroxyphenyl)urea
1-amidino-3-(2,6-dimethyl-3,4-dihydroxyphenyl)urea
1-amidino-3-(2,6-dimethyl-3,4,5-trihydroxyphenyl)urea
1-amidino-3-(2,6-dimethyl-4-methoxyphenyl)urea
1-amidino-3-(2,6-dimethyl-3-methoxyphenyl)urea
1-amidino-3-(2,6-dimethyl-3,4-dimethoxyphenyl)urea
1-amidino-3-(2,6-dimethyl-4-ethoxyphenyl)urea
1-amidino-3-(2,6-dimethyl-3,4-diethoxyphenyl)urea
1-(2,6-dimethyl-4-hydroxyphenyl)-3-methylamidinourea
1-(2,6-dimethyl-3-hydroxyphenyl)-3-methylamidinourea
1-(2,6-dimethyl-3,4-dihydroxyphenyl)-3-methylamidinourea
1-(2,6-dimethyl-4-methoxyphenyl)-3-methylamidinourea
1-(2,6-dimethyl-3-methoxyphenyl)-3-methylamidinourea
1-(2,6-dimethyl-3,4-dimethoxyphenyl)-3-methylamidinourea
1-(2,6-dimethyl-4-ethoxyphenyl)-3-methylamidinourea
1-(2,6-dimethyl-3-ethoxyphenyl)-3-methylamidinourea
1-(2,6-dimethyl-3,4-diethoxyphenyl)-3-methylamidinourea
1-amidino-3-(2,6-dimethylphenyl)urea
1-amidino-3-(2-methyl-6-ethylphenyl)urea
1-amidino-3-(2-ethyl-6-chlorophenyl)urea
1-amidino-3-(2-ethyl-6-bromophenyl)urea
1-amidino-3-(2-ethyl-6-methoxyphenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-(2,6-dichlorophenylamidino)-3-n-propylurea
1-(2,6-dimethylphenyl)-3-(isopropylamidino)urea
1-(4-bromo-3-chloro-6-methylphenyl)-3-methylamidinourea
1-(2-bromo-6-methylphenyl)-3-methylamidinourea
1-(2,6-dimethylphenyl)-3-(N—methyl-N'—propylamidino)urea
1-adamantyl-3-ethylamidinourea
1-phenyl-1-(2-pyridyl)-3-ethylamidinourea
1-(α-napthyl)-3-ethylamidinourea
1-ethyl-3-(α-napthyl)amidinourea
1-(2-pyridyl)-3-methylamidinourea
1-(2-pyridyl)-3-ethylamidinourea
1-(2-pryidyl)-3-propylamidinourea
1-(2-pyridyl)-3-i-propylamidinourea
1-(2-pyridyl)-3-butylamidinourea
1-(2-pyridyl)-3-i-butylamidinourea
1-(2-pyridyl)-3-pentylamidinourea
1-(2-pyridyl)-3-propargylamidinourea
1-(2-pyridyl)-3-allylamidinourea
1-(2-pyridyl)-3-methoxyethylamidinourea
1-(2-pyridyl)-3-benzyloxyethylamidinourea
1-(2-pyridyl)-3-phenethoxyethylamidinourea
1-(2-pyridyl)-3-(N,N—dimethylamidino)urea
1-(2-pyridyl)-3-(N,N—diethylamidino)urea
1-(2-pyridyl)-3-(N,N—tetramethyleneamidino)urea
1-(2-pyridyl)-3-(N,N—pentamethyleneamidino)urea
1-(2-pyridyl)-3-(N,N— hexamethyleneamidino)urea
1-(2-[3-methylpyridyl])-3-methylamidinourea
1-(2-[3-methylpyridyl])-3-ethylamidinourea
1-(2-[3-methylpyridyl])-3-propylamidinourea
1-(2-[3-methylpryidyl])-3-i-propylamidinourea
1-(2-[3-methylpyridyl])-3-i-butylamidinourea
1-(2-[3-methylpyridyl])-3-pentylamidinourea
1-(2-[3-methylpyridyl])-3-allylamidinourea
1-(2-[3-methylpyridyl])-3-propargylamidinourea
1-(2-[3-methylpyridyl])-3-cyclopropylamidinourea
1-(2-[3-methylpryidyl])-3-methoxyethylamidinourea
1-(2-[3-methylpyridyl])-3-benzyloxyethylamidinourea
1-(2-[3-methylpyridyl])-3-(N,N—tetramethyleneamidino)urea
1-(2-[3-methylpyridyl])-3-(N,N—pentamethyleneamidino)urea
1-(2-[3-chloropyridyl])-3-methylamidinourea
1-(2-[3-chloropyridyl])-3-ethylamidinourea
1-(2-[3-chloropyridyl])-3-propylamidinourea
1-(2-[3-chloropyridyl])-3-i-propylamidinourea
1-(2-[3-chloropyridyl])-3-butylamidinourea
1-(2-[3-chloropyridyl])-3-i-butylamidinourea
1-(2-[3-chloropyridyl])-3-t-butylamidinourea
1-(2-[3-chloropyridyl])-3-pentylamidinourea
1-(2-[3-chloropyridyl])-3-allylamidinourea
1-(2-[3-chloropyridyl])-3-propargylamidinourea
1-(2-[3-chloropyridyl])-3-cyclopropylamidinourea
1-(2-[3-chloropyridyl])-3-cyclobutylamidinourea
1-(2-[3-chloropyridyl])-3-cyclopropylmethylamidinourea
1-(2-[3-chloropyridyl])-3-methoxyethylamidinourea
1-(2-[3-chloropyridyl])-3-benzyloxyethylamidinourea
1-(2-[3-chloropyridyl])-3-phenethoxyethylamidinourea
1-(2-[3-chloropyridyl])-3-benzylamidinourea
1-(2-[3-chloropyridyl])-3-(N,N—dimethylamidino)urea
1-(2-[3-chloropyridyl])-3-(N,N—diethylamidino)urea
1-(2-pryidyl)-3-(N,N[3-oxapentamethylene]amidino)urea
1-(3-pyridyl)-3-methylamidinourea
1-(3-pyridyl)-3-ethylamidinourea
1-(3-pyridyl)-3-propylamidinourea
1-(3-pyridyl)-3-i-propylamidinourea
1-(3-pyridyl)-3-butylamidinourea
1-(3-pyridyl)-3-i-butylamidinourea
1-(3-pyridyl)-3-t-butylamidinourea
1-(3-pyridyl)-3-pentylamidinourea
1-(3-pyridyl)-3-allylamidinourea
1-(3-pyridyl)-3-propargylamidinourea
1-(3-pyridyl)-3-cyclobutylamidinourea
1 (3-pyridyl)-3-cyclohexylamidinourea
1-(3-pyridyl)-3-benzylamidinourea
1-(3-pyridyl)-3-methoxyethylamidinourea
1-(3-pyridyl)-3-benzyloxyethylamidinourea
1-(3-pyridyl)-3-methoxyethylamidinourea
1-(3-pyridyl)-3-benzyloxyethylamidinourea
1-(3-pyridyl)-3-phenethoxyethylamidinourea
1-(3-pyridyl)-3-(N,N—diethylamidino)urea
1 (3-pyridyl)-3-(N,N—dimethylamidino)urea
1-(3-pyridyl)-3-(N,N—pentamethyleneamidino)urea
1-(4-pyridyl)-3-methylamidinourea
1-(4-pyridyl)-3-ethylamidinourea
1-(4-pyridyl)-3-propylamidinourea
1-(4-pyridyl)-3-i-propylamidinourea
1-(4-pyridyl)-3-butylamidinourea
1-(4-pyridyl)-3-t-butylamidinourea
1-(4-pyridyl)-3-pentylamidinourea
1-(4-pyridyl)-3-hexylamidinourea
1-(4-pyridyl)-3-propargylamidinourea
1-(4-pyridyl)-3-allylamidinourea
1-(4-pyridyl)-3-methoxyethylamidinourea
1-(4-pyridyl)-3-benzyloxyethylamidinourea
1-(4-pyridyl)-3-phenethoxyethylamidinourea
1-(4-pyridyl)-3-(N,N—tetramethyleneamidino)urea
1-(4-pyridyl)-3-(N,N—pentamethyleneamidino)urea
1-(4-pyridyl)-3-(N,N—hexamethyleneamidino)urea
1-(4-[2-ethylpyridyl])-3-methylamidinourea
1-(4-[2-ethylpyridyl])-3-ethylamidinourea

TABLE I-continued 3-(2-pyridyl-N—oxideamidino)-1-(N,N—dimethyl)urea
3-(2-[3-cyanopyridyl]amidino)-1-methylurea
3-(2-[3-carbomethoxypyridyl]amidino)-1-methylurea
3-(2-[3-carboethoxypyridyl]amidino)-1-methylurea
3-(2-[6-chloropyridyl]amidino)-1-methylurea
3-(2-[6-methylpyridyl]amidino)-1-methylurea
3-(2-[3-ethylpyridyl]amidino)-1-methylurea
3-(3-[2-methylpyridyl]amidino)-1-methylurea
3-(3-[2-ethylpyridyl]amidino)-1-methylurea
3-(3-[2,6-dimethylpyridyl]amidino)-1-methylurea
3-(2-[3-cyanothiophenyl]amidino)-1-methylurea
3-(2-[3-carbomethoxythiophenyl]amidino)-1-methylurea
3-(2-[3-carboethoxythiophenyl]amidino)-1-methylurea
3-(3-[2-methoxypyridyl]amidino)-1-methylurea
3-(3-[2-ethoxypyridyl]amidino)-1-methylurea
3-(3-[2-chloropyridyl]amidino)-1-methylurea
1-(2-furylamidino)urea
1-(3-furylamidino)urea
1-(2-[3-methylfuryl]amidino)urea
3-(2-furylamidino-1-ethylurea
3-(2-furylamidino)-1-propylurea
3-(2-furylamidino)-1-i-propylurea
3-(2-furylamidino)-1-butylurea
3-(2-furylamidino)-1-i-butylurea
3-(2-furylamidino)-1-sec-butylurea
3-(2-furylamidino)-1-t-butylurea
3-(2-furylamidino)-1-propargylurea
3-(4-pyridylamidino)-1-allylurea
3-(4-pyridylamidino)-1-methoxyethylurea
3-(4-pyridylamidino)-1-benzyloxyethylurea
3-(4-pyridylamidino)-1-phenethoxyethylurea
3-(4-pyridylamidino)-1-(N,N—dimethyl)urea
3-(4-pyridylamidino)-1-(N,N—diethyl)urea
3-(4-pyridylamidino)-1-(N—methyl-N—ethyl)urea
3 (4-pyridylamidino)-1-(N,N—tetramethylene)urea
3-(4-pyridylamidino)-1-(N,N—pentamethylene)urea
3-(4-pyridylamidino)-1-(N,N—hexamethylene)urea
3-(4-[2-ethylpyridyl]amidino)-1-methylurea
3-(4-[2-ethylpyridyl]amidino)-1-ethylurea
3-(4-[2-ethylpyridyl]amidino)-1-propylurea
3-(4-[2-ethylpyridyl]amidino)-1-butylurea
3-(4-[2-ethylpyridyl]amidino)-1-i-butylurea
3-(4-[2-ethylpyridyl]amidino)-1-pentylurea
3-(4-[2-ethylpyridyl]amidino)-1-allylurea
3-(4-[2-ethylpyridyl]amidino)-1-propargylurea
3-(4-[2-ethylpyridyl]amidino)-1-methoxyethylurea
3-(4-[2-ethylpyridyl]amidino)-1-benzyloxyethylurea
3-(4-[2-ethylpyridyl]amidino)-1-(N,N—dimethyl)urea
3-(4-[2-ethylpyridyl]amidino)-1-(N,N—diethyl)urea
3-(4-[2,6-dichloropyridyl]amidino)-1-methylurea
3-(4-[2,6-dimethylpyridyl]amidino)-1-methylurea
3-(4-[2-methyl,6-chloropyridyl]amidino)-1-methylurea
3-(2-thiophenylamidino)-1-methylurea
3-(3-thiophenylamidino)-1-methylurea
3-(3-pyridylamidino)-1-methylurea
3-(3-pyridylamidino)-1-ethylurea
3-(3-pyridylamidino)-1-propylurea
3-(3-pyridylamidino)-1-propylurea
3-(3-pyridylamidino-1-butylurea
3-(3-pyridylamidino)-1-i-butylurea
3-(3-pyridylamidino)-1-t-butylurea
3-(3-pyridylamidino)-1-pentylurea
3-(3-pyridylamidino)-1-allylurea
3-(3-pyridylamidino)-1-propargylurea
3-(3-pyridylamidino)-1-cyclobutylurea
3-(3-pyridylamidino)-1-cyclohexylurea
3-(3-pyridylamidino)-1-benzylurea
3-(3-pyridylamidino)-1-methoxyethylurea
3-(3-pyridylamidino)-1-benzyloxyethylurea
3-(3-pyridylamidino)-1-methoxyethylurea
3-(3-pyridylamidino)-1-benzyloxyethylurea
3-(3-pyridylamidino)-1-phenethoxyethylurea
3-(3-pyridylamidino)-1-(N,N—diethyl)urea
3-(3-pyridylamidino)-1-(N,N—dimethyl)urea
3-(3-pyridylamidino)-1-(N,N—pentamethylene)urea
3-(4-pyridylamidino)-1-methylurea
3-(4-pyridylamidino)-1-ethylurea
3-(4-pyridylamidino)-1-propylurea
3-(4-pyridylamidino)-1-i-propylurea
3-(4-pyridylamidino)-1-butylurea
3-(4-pyridylamidino)-1-t-butylurea
3-(4-pyridylamidino)-1-pentylurea

TABLE I-continued 3-(2-[3-methylpyridyl]amidino)-1-phenethoxyethylurea
3-(2-[3-methylpyridyl]amidino)-1-benzylurea
3-(2-[3-methylpyridyl]amidino)-1-(N,N—dimethyl)urea
3-(2-[3-methylpyridyl]amidino)-1-(N,N—diethyl)urea
3-(2-[3-methylpyridyl]amidino)-1-(N,N—tetramethylene)urea
3-(2-[3-methylpyridyl]amidino)-1-(N,N—pentamethylene)urea
3-(2-[3-chloropyridyl]amidino)-1-methylurea
3-(2-[3-chloropyridyl]amidino)-1-ethylurea
3-(2-[3-chloropyridyl]amidino)-1-propylurea
3-(2-[3-chloropyridyl]amidino)-1-i-propylurea
3-(2-[3-chloropyridyl]amidino)-1-butylurea
3-(2-[3-chloropyridyl]amidino)-1-i-butylurea
3-(2-[3-chloropyridyl]amidino)-1-t-butylurea
3-(2-[3-chloropyridyl]amidino)-1-pentylurea
3-(2-[3-chloropyridyl]amidino)-1-allylurea
3-(2-[3-chloropyridyl]amidino)-1-propargylurea
3-(2-[3-chloropyridyl]amidino)-1-cyclopropylurea
3-(2-[3-chloropyridyl]amidino)-1-cyclobutylurea
3-(2-[3-chloropyridyl]amidino)-1-cyclopropylmethylurea
3-(2-[3-chloropyridyl]amidino)-1-methoxyethylurea
3-(2-[3-chloropyridyl]amidino)-1-benzyloxyethylurea
3-(2-[3-chloropyridyl]amidino)-1-phenethoxyethylurea
3-(2-[3-chloropyridyl]amidino)-1-benzylurea
3-(2-[3-chloropyridyl]amidino)-1-(N,N—dimethyl)urea
3-(2-pyridylamidino)-1-methylurea
3-(2-pyridylamidino)-1-ethylurea
3-(2-pyridylamidino)-1-propylurea
3-(2-pyridylamidino)-1-i-propylurea
3-(2-pyridylamidino)-1-butylurea
3-(2-pyridylamidino)-1-i-butylurea
3-(2-pyridylamidino)-1-pentylurea
3-(2-pyridylamidino)-1-propargylurea
3-(2-pyridylamidino)-1-allylurea
3-(2-pyridylamidino)-1-methoxyethylurea
3-(2-pyridylamidino)-1-benzyloxyethylurea
3-(2-pyridylamidino)-1-phenethoxyethylurea
3-(2-pyridylamidino)-1-(N,N—dimethyl)urea
3-(2-pyridylamidino)-1-(N,N—diethyl)urea
3-(2-pyridylamidino)-1-(N,N— tetramethylene)urea
3-(2-pyridylamidino)-1-(N,N—pentamethylene)urea
3-(2-pyridylamidino)-1-(N,N—hexamethylene)urea
3-(2-[3-methylpyridyl]amidino)-1-methylurea
3-(2-[3-methylpyridyl]amidino)-1-ethylurea
3-(2-[3-methylpyridyl]amidino)-1-propylurea
3-(2-[3-methylpryidyl]amidino)-1-i-propylurea
3-(2-[3-methylpyridyl]amidino)-1-i-butylurea
3-(2-[3-methylpyridyl]amidino)-1-pentylurea
3-(2-[3-methylpyridyl]amidino)-1-allylurea
3-(2-[3-methylpyridyl]amidino)-1-propargylurea
3-(2-[3-methylpyridyl]amidino)-1-cyclopropylurea
3-(2-[3-methylpyridyl]amidino)-1-methoxyethylurea
1-(2'-pyridylmethyl)-3-methylamidinourea
1-(2'-pyridylmethyl)-3-ethylamidinourea
1-(2'-pryidylmethyl)-3-propylamidinourea
1-(2'-pyridylmethyl)-3-i-propylamidinourea
1-(2'-pyridylmethyl)-3-butylamidinourea
1-(2'-pyridylmethyl)-3-i-butylamidinourea
1-(2'-pyridylmethyl)-3-pentylamidinourea
1-(2'-pyridylmethyl)-3-propargylamidinourea
1-(2'-pyridylmethyl)-3-allylamidinourea
1-(2'-pyridylmethyl)-3-methoxyethylamidinourea
1-(2'-pyridylmethyl)-3-benzyloxyethylamidinourea
1-(2'-pyridylmethyl)-3-phenethoxyethylamidinourea
1-(2'-pyridylmethyl)-3-(N,N—dimethylamidino)urea
1-(2'-pyridylmethyl)-3-(N,N—diethylamidino)urea
1-(2'-pyridylmethyl)-3-(N,N—tetramethyleneamidino)urea
1-(2'-pyridylmethyl)-3-(N,N—pentamethyleneamidino)urea
1-(2'-pyridylmethyl)-3-(N,N—hexamethyleneamidino)urea
1-(3'-methyl-2'-pyridylmethyl)-3-methylamidinourea
1-(3'-methyl-2'-pyridylmethyl)-3-ethylamidinourea
1-(3'-methyl-2'-pyridylmethyl)-3-propylamidinourea
1-(3'-methyl-2'-pyridylmethyl)-3-i-propylamidinourea
1-(3'-methyl-2'-pyridylmethyl)-3-i-butylamidinourea
1-(3'-methyl-2'-pyridylmethyl)-3-pentylamidinourea
1-(3'-methyl-2'-pyridylmethyl)-3-allylamidinourea
1-(3'-methyl-2'-pyridylmethyl)-3-propargylamidinourea
1-(3'-methyl-2'-pyridylmethyl)-3-cyclopropylamidinourea
1-(3'-methyl-2'-pyridylmethyl)-3-methoxyethylamidinourea
1-(3'-methyl-2'-pyridylmethyl)-3-benzyloxyethylamidinourea
1-(3'-pyridylmethyl)-3-t-butylamidinourea
1-(3'-pyridylmethyl)-3-pentylamidinourea
1-(3'-pyridylmethyl)-3-allylamidinourea TABLE I-continued 1-(4-[2-ethylpyridyl])-3-propylamidinourea
1-(4-[2-ethylpyridyl])-3-butylamidinourea
1-(4-[2-ethylpyridyl])-3-i-butylamidinourea
1-(4-[2-ethylpyridyl])-3-pentylamidinourea
1-(4-[2-ethylpyridyl])-3-allylamidinourea
1-(4-[2-ethylpyridyl])-3-propargylamidinourea
1-(4-[2-ethylpyridyl])-3-methoxyethylamidinourea
1-(4-[2-ethylpyridyl])-3-benzyloxyethylamidinourea
1-(4-[2-ethylpyridyl])-3-(N,N—dimethylamidino)urea
1-(4-[2-ethylpyridyl])-3-(N,N—diethylamidino)urea
1-(4-[2-ethylpyridyl] )-3-(N,N—tetramethyleneamidino)urea
1-(3[2,4-dimethylthiophenyl])-3-amidinourea
1-(3[2-chloro-4-methylthiophenyl])-3-methylamidinourea
1-(4-[2,6-dichloropyridyl])-3-methylamidinourea
1-(4-[2,6-dimethylpyridyl])-3-methylamidinourea
1-(4-[2-methyl-6-chloropyridyl])-3-methylamidinourea
1-(2-thiophenyl)-3-methylamidinourea
1-(3-thiophenyl)-3-methylamidinourea
1-(2-[3-methylthiophenyl])-3-methylamidinourea
1-(2-[3-chlorothiophenyl])-3-methylamidinourea
1-(2-pyridyl-N—oxide)-3-(N,N—dimethylamidino)urea
1-(2-[3-cyanopyridyl])-3-methylamidinourea
1-(2-[3-carbomethoxypyridyl])-3-methylamidinourea
1-(2-[3-carboethoxypyridyl])-3-methylamidinourea
1-(2-[6-chloropyridyl])-3-methylamidinourea
1-(3-[2-methylpyridyl])-3-methylamidinourea
1-(3-[2-ethylpyridyl])-3-methylamidinourea
1-(3-[2,-dimethylpyridyl])-3-methylamidinourea
1-(2-[3-cyanothiophenyl])-3-methylamidinourea
1-(2-[3-carbomethoxythiophenyl])-3-methylamidinourea
1-(2-[3-carboethoxythiophenyl])-3-methylamidinourea
1-(3-[2-methoxypyridyl])-3-methylamidinourea
1-(3-[2-ethoxypyridyl])-3-methylamidinourea
1-(3-[2-chloropyridyl])-3-methylamidinourea
1-(2-furyl)-3-amidinourea
1-(3-furyl)-3-amidinourea
1-(2-[3-methylfuryl])-3-amidinourea
1-(2-furyl)-3-ethylamidinourea
1-(2-furyl)-3-propylamidinourea
1-(2-furyl)-3-i-propylamidinourea
1-(2-furyl)-3-butylamidinourea
1-(2-furyl)-3-i-butylamidinourea
1-(2-furyl)-3-sec-butylamidinourea
1-(2-furyl)-3-t-butylamidinourea
1-(2-furyl)-3-pentylamidinourea
1-(2-furyl)-3-hexylamidinourea
1-(2-furyl)-3-heptylamidinourea
1-(2-furyl)-3-cyclopropylamidinourea
1-(2-furyl)-3-cyclobutylamidinourea
1-(2-pyridyl-N—oxide)-3-methylamidinourea
1-(3-pyridyl-N—oxide)-3-methylamidinourea
1-(4-pyridyl-N—oxide)-3-methylamidinourea
1-(2-furyl)-3-methylamidinourea
1-(1-imidazolyl)-3-methylamidinourea
1-(2-imidazolyl)-3-methylamidinourea
1-(4-imidazolyl)-3-methylamidinourea
1-(2-oxazolyl)-3-methylamidinourea
1-(4-oxazolyl)-3-methylamidinourea
1-(5-oxazolyl)-3-methylamidinourea
1-(1-pyrazolyl)-3-methylamidinourea
1-(1-[3-pyrrolidyl)-3-methylamidinourea
1-(2-pyrrolyl)-3-methylamidinourea
1-(1-morpholinyl)-3-methylamidinourea
1-(2-morpholinyl)-3-methylamidinourea
1-(2-pyrimidinyl)-3-methylamidinourea
1-(4-pyrimidinyl)-3-methylamidinourea
1-(2-quinolinyl)-3-methylamidinourea
1-(4-quinolinyl)-3-methylamidinourea
1-(1-isoquinolinyl)-3-methylamidinourea
1-(2-furyl)-3-cyclopentylamidinourea
1-(2-furyl)-3-cyclohexylamidinourea
1-(2-furyl)-3-phenylamidinourea
1-(2-furyl)-3-benzylamidinourea
1-(2-furyl)-3-phenethylamidinourea
1-(2-furyl)-3-(N—methyl-N—benzylamidino)urea
1-(2-furyl)-3-(N,N—dibenzylamidino)urea
1-(2-tetrahydrofuryl)-3-amidinourea
1-(2-[3-methyltetrahydrofuryl])-3-amidinourea
1-(3-tetrahydrofuryl)-3-amidinourea
1-(3-[2-methyltetrahydrofuryl])-3-amidinourea
1-(1-imidazolyl)-3-amidinourea
1-(2-[3-pyrrolino]amidino)urea
1-(1-[2-methyl-3-pyrrolino]amidino)urea
1-(1-[3-methyl-2-pyrrolino]amidino)urea
1-(1-pyrrolidinoamidino)urea
1-(1-[2-methylpyrrolidino]amidino)urea
1-(2-pyrrolidinoamidino)urea
1-(2-[1-methylpyrrolidino]amidino)urea
1-(1-morpholinoamidino)urea
1-(1-[2-methylmorpholino]amidino)urea
1-(2-morpholinoamidino)urea
1-(2-[1-methylmorpholino]amidino)urea
1-(2-[3-methylmorpholino]amidino)urea
1-(2-[1-[3-methylmorpholino]amidino)urea
1-(3-morpholinoamidino)urea
1-(3-[1-methylmorpholino]amidino)urea
1-(3-[2-methylmorpholino]amidino)urea
1-(2-pyrimidinoamidino)urea
1-(2-[4-methylpyrimidino]amidino)urea
1-(4-pyrimidinoamidino)urea
1-(4-[2-methylpyrimidino]amidino)urea
1-(2-quinolinoamidino)urea
1-(2-[3-methylquinolino]amidino)urea
1-(4-quinolinoamidino)urea
1-(4-[2-methylquinolino]amidino)urea
1-(4-[3-methylquinolino]amidino)urea
1-(1-isoquinolinoamidino)urea
3-(2-furylamidino)-1-cyclopentylurea
3-(2-furylamidino)-1-cyclohexylurea
3-(2-furylamidino)-1-phenylurea
3-(2-furylamidino)-1-benzylurea
3-(2-furylamidino)-1-phenethylurea
3-(2-furylamidino)-1-(N—methyl-N—benzyl)urea
3-(2-furylamidino)-1-(N,N—dibenzyl)urea
1-(2-tetrahydrofurylamidino)urea
1-(2-[3-methyltetrahydrofuryl]amidino)urea
1-(3-tetrahydrofurylamidino)urea
1-(3-[2-methyltetrahydrofuryl]amidino)urea
1-(1-imidazoalamidino)urea
1-(1-[2-methylimidazoal]amidino)urea
1-(4-imidazoalamidino)urea
1-(4-[1-methylimidazoal]amidino)urea
1-(4-[2-methylimidazoal]amidino)urea
1-(2-imidazoalamidino)urea
1-(2-oxazoalamidino)urea
1-(2-[4-methyloxazoal]amidino)urea
1-(4-oxazoalamidino)urea
1-(4-[2-methyloxazoal]amidino)urea
1-(5-oxazoalamidino)urea
1-(5-[2-methyloxazoal]amidino)urea
1-(4-thiazoalamidino)urea
1-(4-[5-methylthiazoal]amidino)urea
1-(5-thiazoalamidino)urea
1-(5-[4-methylthiazoal]amidino)urea
1-(pyrazoalamidino)urea
3-(2-furylamino)-1-heptylurea
3-(2-furylamidino)-1-cyclopropylurea
3-(2-furylamidino)-1-cyclobutylurea
3-(2-pyridyl-N—oxideamidino)-1-methylurea
3-(2-pyridyl-N—oxideamidino)-1-methylurea
3-(4-pyridyl-N—oxideamidino)-1-methylurea
3-(2-furylamidino)-1-methylurea
3-(3-furylamidino)-1-methylurea
3-(2-tetrahydrofurylamidino)-1-methylurea
3-(3-tetrahydrofurylamidino)-1-methylurea
3-(1-imidazoalamidino)-1-methylurea
3-(2-imidazoalamidino)-1-methylurea
3-(4-imidazoalamidino)-1-methylurea
3-(2-oxazoalamidino)-1-methylurea
3-(4-oxazoalamidino)-1-methylurea
3-(5-oxazoalamidino)-1-methylurea
3-(2-thiazoalamidino)-1-methylurea
3-(4-thiazoalamidino)-1-methylurea
3-(5-thiazoalamidino)-1-methylurea
3-(1-pyrazoalamidino)-1-methylurea
3-(1-[3-pyrrolino] amidino)-1-methylurea
3-(2-pyrrolinoamidino)-1-methylurea
3-(1-morpholinoamidino)-1-methylurea
3-(2-morpholinoamidino)-1-methylurea
3-(2-pyrimidinoamidino)-1-methylurea
3-(4-pyrimidinoamidino)-1-methylurea
3-(2-quinolinoamidino)-1-methylurea
3-(4-quinolinoamidino)-1-methylurea
3-(2-[5-chlorothiophenyl]amidino)-3-methylurea

TABLE I-continued 1-(3'-pyridylmethyl)-3-propargylamidinourea
1-(3'-pyridylmethyl)-3-cyclobutylamidinourea
1-(3'-pyridylmethyl)-3-cyclohexylamidinourea
1-(3'-pyridylmethyl)-3-benzylamidinourea
1-(3'-pyridylmethyl)-3-methoxyethylamidinourea
1-(3'-pyridylmethyl)-3-benzyloxyethylamidinourea
1-(3'-pyridylmethyl)-3-methoxyethylamidinourea
1-(3'-pyridylmethyl)-3-benzyloxyethylamidinourea
1-(3'-pyridylmethyl)-3-phenethoxyethylamidinourea
1-(3'-pyridylmethyl)-3-(N,N—dimethylamidino)urea
1-(3'-pyridylmethyl)-3-(N,N—diethylamidino)urea
1-(3'-pyridylmethyl)-3-(N,N—pentamethyleneamidino)urea
1-(4'-pyridylmethyl)-3-methylamidinourea
1-(4'-pyridylmethyl)-3-ethylamidinourea
1-(4'-pyridylmethyl)-3-propylamidinourea
1-(4'-pyridylmethyl)-3-i-propylamidinourea
1-(4'-pyridylmethyl)-3-butylamidinourea
1-(4'-pyridylmethyl)-3-t-butylamidinourea
1-(4'-pyridylmethyl)-3-pentylamidinourea
1-(4'-pyridylmethyl)-3-hexylamidinourea
1-(4'-pyridylmethyl)-3-propargylamidinourea
1-(4'-pyridylmethyl)-3-allylamidinourea
1-(4'-pyridylmethyl)-3-methoxyethylamidinourea
1-(4'-pyridylmethyl)-3-benzyloxyethylamidinourea
1-(4'-pyridylmethyl)-3-phenethoxyethylamidinourea
1-(4'-pyridylmethyl)-3-(N,N—tetramethyleneamidino) urea
1-(4'-pyridylmethyl)-3-(N,N—pentamethyleneamidino)urea
1-(4'-pyridylmethyl)-3-(N,N—hexamethyleneamidino)urea
1-(2'-ethyl-4'-pyridylmethyl)-3-methylamidinourea
1-(2'-ethyl-4'-pyridylmethyl)-3-ethylamidinourea
1-(2'-ethyl-4'-pyridylmethyl)-3-propylamidinourea
1-(2' -ethyl-4'-pyridylmethyl)-3-butylamidinourea
1-(2'-ethyl-4'-pyridylmethyl)-3-i-butylamidinourea
1-(2'-ethyl-4'-pyridylmethyl)-3-pentylamidinourea
1-(2'-ethyl-4'-pyridylmethyl)-3-allylamidinourea
1-(2'-ethyl-4'-pyridylmethyl)-3-propargylamidinourea
1-(2'-ethyl-4'-pyridylmethyl)-3-methoxyethylamidinourea
1-(2'-ethyl-4'-pyridylmethyl)-3-benzyloxyethylamidinourea
1-(2'-ethyl-4'-pyridylmethyl)-3-(N,N—dimethylamidino)urea
1-(2'-ethyl-4'-pyridylmethyl)-3-(N,N—diethylamidino)urea
1-(2',6'-dichloro-4'-pyridylmethyl)-3-methylamidinourea
1-(2',6'-dimethyl-4'-pyridylmethyl)-3-methylamidinourea
1-(2'-thiophenylmethyl)-3-methylamidinourea
1-(3'-thiophenylmethyl)-3-methylamidinourea
1-(5'-methyl-2'-thiophenylmethyl)-3-methylamidinourea
1-(5'-chloro-2'-thiophenylmethyl)-3-methylamidinourea
1-(2'-pyridylmethyl-N—oxide)-3-(N,N—dimethylamidino)urea
1-(3'-cyano-2'-pyridylmethyl)-3-methylamidinourea
1-(3'-carbomethoxy-2'-pyridylmethyl-3-methylamidinourea
1-(3'-carboethoxy-2'-pyridylmethyl)-3-methylamidinourea
1-(6'-chloro-2'-pyridylmethyl)-3-methylamidinourea
1-(6'-methyl-2'-pyridylmethyl)-3-methylamidinourea
1-(3'-ethyl-2'-pyridylmethyl)-3-methylamidinourea
1-(1'-imidazolylmethyl)-3-methylamidinourea
1-(2'-imidazolylmethyl)-3-methylamidinourea
1-(4'-imidazolylmethyl)-3-methylamidinourea
1-(2'-oxazolylmethyl)-3-methylamidinourea
1-(4'-oxazolylmethyl)-3-methylamidinourea
1-(5'-oxazolylmethyl)-3-methylamidinourea
1-(2'-thiazolylmethyl)-3-methylamidinourea
1-(4'-thiazolylmethyl)-3-methylamidinourea
1-(5'-thiazolylmethyl)-3-methylamidinourea
1-(1'-pyrazolylmethyl)-3-methylamidinourea
1-(3'-pyrrolidinylmethyl)-3-methylamidinourea
1-(2'-pyrrolidinylmethyl)-3-methylamidinourea
1-(4'-morpholinylmethyl)-3-methylamidinourea
1-(2'-morpholinylmethyl)-3-methylamidinourea
1-(2'-pyrimidinylmethyl)-3-methylamidinourea
1-(4'-pyrimidinylmethyl)-3-methylamidinourea
1-(2'-quinolylmethyl)-3-methylamidinourea
1-(4'-quinolylmethyl)-3-methylamidinourea
1-(1'-isoquinolylmethyl)-3-methylamidinourea
1-(furfuryl-3-cyclopenylamidinourea
1-(furfuryl-3-cyclohexylamidinourea
1-(furfuryl-3-phenylamidinourea
1-(furfuryl-3-benzylamidinourea
1-(furfuryl-3-phenethylamidinourea
1-furfuryl-3-(N—methyl-N—benzylamidino)urea
1-furfuryl-3-(N,N—dibenzylamidino)urea
1-tetrahydrofurfuryl-3-amidinourea
1-(4'-imidazolylmethyl)-3-amidinourea
1-(1'-methyl-4'-imidazolylmethyl)-3-amidinourea
1-(2'-methyl-4'-imidazolylmethyl)-3-amidinourea
1-(2'-imidazolylmethyl)-3-amidinourea
1-(2'-oxazolylmethyl)-3-amidinourea
1-(4'-methyl-2'-oxazolylmethyl)-3-amidinourea
1-(4'-oxazolylmethyl)-3-amidinourea
1-(4'-methyl-2'-oxazolylmethyl)-3-amidinourea
1-(4'-oxazolylmethyl)-3-amidinourea
1-(2'-methyl-4'-oxazolylmethyl)-3-amidinourea
1-(5'-oxazolylmethyl)-3-amidinourea
1-(2'-methyl-5'-oxazolylmethyl)-3-amidinourea
1-(4'-thiazolylmethyl)-3-amidinourea
1-(5'-methyl-4'-thiazolylmethyl)-3-amidinourea
1-(5'-thiazolylmethyl)-3-amidinourea
1-(4'-methyl-5'-thiazolylmethyl)-3-amidinourea
1-(1'-pyrazolylmethyl)-3-amidinourea
1-(3'-pyrrolylmethyl)-3-amidinourea
1-(2'-methyl-3'-pyrrolylmethyl)-3-amidinourea
1-(3'-methyl-2'-pyrrolylmethyl)-3-amidinourea
1-(1'-pyrrolidinylmethyl)-3-amidinourea
1-(2'-methyl-1'-pyrrolidinylmethyl)-3-amidinourea
1-(1'-methyl-2'-pyrrolidinylmethyl)-3-amidinourea
1-(4'-morpholinylmethyl)-3-amidinourea
1-(2'-methyl-4'-morpholinylmethyl)-3-amidinourea
1-(2'-morpholinylmethyl)-3-amidinourea
1-(4'-methyl-2'-morpholinylmethyl)-3-amidinourea
1-(3'-methyl-2'-morpholinylmethyl)-3-amidinourea
1-[2-(2'-pyridyl)ethyl]-3-methylamidinourea
1-[2-(2'-pyridyl)ethyl]-3-ethylamidinourea
1-[2-(2'-pryidyl)ethyl]-3-propylamidinourea
1-[2-(2'-pyridyl)ethyl]-3-i-propylamidinourea
1-[2-(2'-pyridyl)ethyl]-3-butylamidinourea
1-[2-(2'-pyridyl)ethyl]-3-i-butylamidinourea
1-[2-(2'-pyridyl)ethyl]-3-pentylamidinourea
1-[2-(2'-pyridyl)ethyl]-3-propargylamidinourea
1-[2-(2'-pyridyl)ethyl]-3-allylamidinourea
1-[2-(2'-pyridyl)ethyl]-3-methoxyethylamidinourea
1-[2-(2'-pyridyl)ethyl]-3-benzyloxyethylamidinourea
1-[2-(2'-pyridyl)ethyl]-3-phenethoxyethylamidinourea
1-[2-(2'-pyridyl)ethyl]-3-(N,N—dimethylamidino)urea
1-[2-(2'-pyridyl)ethyl]-3-(N,N—diethylamidino)urea
1-[2-(2'-pyridyl)ethyl]-3-(N,N—tetramethyleneamidino)urea
1-[2-(2'-pyridyl)ethyl]-3-(N,N—pentamethyleneamidino)urea
1-[2-(2'-pyridyl)ethyl]-3-(N,N—hexamethyleneamidino)urea
1-[2-(3'-methyl-2'-pyridyl)ethyl]-3-methylamidinourea
1-[2-(3'-methyl-2'-pyridyl)ethyl]-3-ethylamidinourea
1-[2-(3'-methyl-2'-pyridyl)ethyl]-3-propylamidinourea
1-[2-(3'-methyl-2'-pyridyl)ethyl]-3-i-propylamidinourea
1-[2-(3'-methyl-2'-pyridyl)ethyl]-3-i-butylamidinourea
1-[2-(3'-methyl-2'-pyridyl)ethyl]-3-pentylamidinourea
1-[2-(3'-methyl-2'-pyridyl)ethyl]-3-allylamidinourea
1-[2-(3'-methyl-2'-pyridyl)ethyl]-3-propargylamidinourea
1-[2-(3'-pyridyl)ethyl]-3-t-butylamidinourea
1-[2-(3'-pyridyl)ethyl]-3-pentylamidinourea
1-[2-(3'-pyridyl)ethyl]-3-allylamidinourea
1-[2-(3'-pyridyl)ethyl]-3-propargylamidinourea
1-[2-(3'-pyridyl)ethyl]-3-cyclobutylamidinourea
1-[2-(3'-pyridyl)ethyl]-3-cyclohexylamidinourea
1-[2-(3'-pyridyl)ethyl]-3-benzylamidinourea
1-[2-(3'-pyridyl)ethyl]-3-methoxyethylamidinourea
1-[2-(3'-pyridyl)ethyl]-3-benzyloxyethylamidinourea
1-[2-(3'-pyridyl)ethyl]-3-methoxyethylamidinourea
1-[2-(3'-pyridyl)ethyl]-3-benzyloxyethylamidinourea
1-[2-(3'-pyridyl)ethyl]-3-phenethoxyethylamidinourea
1-[2-(3'-pyridyl)ethyl]-3-(N,N—dimethylamidino)urea
1-[2-(3'-pyridyl)ethyl]-3-(N,N—diethylamidino)urea
1-[2-(4'-pyridyl)ethyl]-3-methylamidinourea
1-[2-(4'-pyridyl)ethyl]-3-ethylamidinourea
1-[2-(4'-pyridyl)ethyl]-3-propylamidinourea
1-[2-(4'-pyridyl)ethyl]-3-i-propylamidinourea
1-[2-(4'-pyridyl)ethyl]-3-butylamidinourea
1-[2-(4'-pyridyl)ethyl]-3-t-butylamidinourea
1-[2-(4'-pyridyl)ethyl]-3-pentylamidinourea
1-[2-(4'-pyridyl)ethyl]-3-hexylamidinourea
1-[2-(4'-pyridyl)ethyl]-3-propargylamidinourea
1-[2-(4'-pyridyl)ethyl]-3-allylamidinourea
1-[2-(4'-pyridyl)ethyl]-3-methoxyethylamidinourea
1-[2-(4'-pyridyl)ethyl]-3-benzyloxyethylamidinourea
1-[2-(4'-pyridyl)ethyl]-3-phenethoxyethylamidinourea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea

TABLE I-continued

1-[3-(2'-pyridyl)propyl]-3-butylamidinourea
1-[3-(2'-pyridyl)propyl]-3-i-butylamidinourea
1-[3-(2'-pyridyl)propyl]-3-pentylamidinourea
1-[3-(2'-pyridyl)propyl]-3-propargylamidinourea
1-[3-(2'-pyridyl)propyl]-3-allylamidinourea
1-[3-(2'-pyridyl)propyl]-3-methoxyethylamidinourea
1-[3-(2'-pyridyl)propyl]-3-benzyloxyethylamidinourea
1-[3-(2'-pyridyl)propyl]-3-phenethoxyethylamidinourea
1-[3-(2'-pyridyl)propyl]-3-(N,N—dimethylamidino)urea
1-[3-(2'-pyridyl)propyl]-3-(N,N—diethylamidino)urea
1-[3-(2'-pyridyl)propyl]-3-(N,N—tetramethyleneamidino)urea
1-[3-(2'-pyridyl)propyl]-3-(N,N—pentamethyleneamidino)urea
1-[3-(2'-pyridyl)propyl]-3-(N,N—hexamethyleneamidino)urea
1-[3-(3'-methyl-2'-pyridyl)propyl]-3-methylamidinourea
1-[3-(3'-methyl-2'-pyridyl)propyl]-3-ethylamidinourea
1-[3-(3'-methyl-2'-pyridyl)propyl]-3-propylamidinourea
1-[3-(3'-methyl-2'-pyridyl)propyl]-3-i-propylamidinourea
1-[3-(3'-methyl-2'-pyridyl)propyl]-3-i-butylamidinourea
1-[3-(3'-methyl-2'-pyridyl)propyl]-3-pentylamidinourea
1-[3-(3'-methyl-2'-pyridyl)propyl]-3-allylamidinourea
1-[3-(3'-methyl-2'-pyridyl)propyl]-3-propargylamidino
1-[3-(3'-pyridyl)propyl]-3-t-butylamidinourea
1-[3-(3'-pyridyl)propyl]-3-pentylamidinourea
1-[3-(3'-pyridyl)propyl]-3-allylamidinourea
1-[3-(3'-pyridyl)propyl]-3-propargylamidinourea
1-[3-(3'-pyridyl)propyl]-3-cyclobutylamidinourea
1-[3-(3'-pyridyl)propyl]-3-cyclohexylamidinourea
1-[3-(3'-pyridyl)propyl]-3-benzylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-phenethoxyethylamidinourea
1-[3-(3'-pyridyl)propyl]-3-(N,N—dimethylamidino)urea
1-[3-(3'-pyridyl)propyl]-3-(N,N—diethylamidino)urea
1-[3-(3'-pyridyl)propyl]-3-(N,N—pentamethyleneamidino)urea
1-[3-(4'-pyridyl)propyl]-3-methylamidinourea
1-[3-(4'-pyridyl)propyl]-3-ethylamidinourea
1-[3-(4'-pyridyl)propyl]-3-propylamidinourea
1-[3-(4'-pyridyl)propyl]-3-i-propylamidinourea
1-[3-(4'-pyridyl)propyl]-3-butylamidinourea
1-[3-(4'-pyridyl)propyl]-3-t-butylamidinourea
1-[3-(4'-pyridyl)propyl]-3-pentylamidinourea
1-[3-(4'-pyridyl)propyl] -3-hexylamidinourea
1-[3-(4'-pyridyl)propyl]-3-propargylamidinourea
1-[3-(4'-pyridyl)propyl]-3-allylamidinourea
1-[3-(4'-pyridyl)propyl]-3-methoxyethylamidinourea
1-[3-(4'-pyridyl)propyl]-3-benzyloxyethylamidinourea
1-[3-(4'-pyridyl)propyl]-3-phenethoxyethylamidinourea
1-[3-(3'-pryidyl)propyl]-3-t-butylamidinourea
1-[3-(3'-pyridyl)propyl]-3-pentylamidinourea
1-[3-(3'-pyridyl)propyl]-3-allylamidinourea
1-[3-(3'-pyridyl)propyl]-3-propargylamidinourea
1-[3-(3'-pyridyl)propyl]-3-cyclobutylamidinourea
1-[3-(3'-pyridyl)propyl]-3-cyclohexylamidinourea
1-[3-(3'-pyridyl)propyl]-3-benzylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-phenethoxyethylamidinourea
1-[3-(3'-pyridyl)propyl]-3-(N,N—dimethylamidino)urea
1-[3-(3'-pyridyl)propyl]-3-(N,N—diethylamidino)urea
1-[3-(4'-pyridyl)propyl]-3-methylamidinourea
1-[3-(4'-pyridyl)propyl]-3-ethylamidinourea
1-[3-(4'-pyridyl)propyl]-3-propylamidinourea
1-[3-(4'-pyridyl)propyl]-3-i-propylamidinourea
1-[3-(4'-pyridyl)propyl]-3-butylamidinourea
1-[3-(4'-pyridyl)propyl]-3-t-butylamidinourea
1-[3-(4'-pyridyl)propyl]-3-pentylamidinourea
1-[3-(4'-pyridyl)propyl]-3-hexylamidinourea
1-[3-(4'-pyridyl)propyl]-3-propargylamidinourea
1-[3-(4'-pyridyl)propyl]-3-allylamidinourea
1-[3-(4'-pyridyl)propyl]-3-methoxyethylamidinourea
1-[3-(4'-pyridyl)propyl]-3-benzyloxyethylamidinourea
1-[3-(4'-pyridyl)propyl]-3-phenethoxyethylamidinourea
1-[3-(4'-pyridyl)propyl]-3-(N,N—dimethylamidino)urea
1-(2'-methyl-3'-morpholinylmethyl)-3-amidinourea
1-(2'-pyrimidinylmethyl)-3-amidinourea
1-(4'-methyl-2'-pyrimidinylmethyl)-3-amidinourea
1-(4'-pyrimidinylmethyl)-3-amidinourea
1-(2'-methyl-4'-pyrimidinylmethyl)-3-amidinourea

TABLE I-continued 1-(2'-quinolylmethyl)-3-amidinourea
1-(3'-methyl-2'-quinolylmethyl)-3-amidinourea
1-(4'-quinolylmethyl)-3-amidinourea
1-(3'-methyl-4'-quinolylmethyl)-3-amidinourea
1-(1'-isoquinolylmethyl)-3-amidinourea
1-(3'-morpholinylmethyl)-3-amidinourea
1-(4'-methyl-3'-morpholinylmethyl)-3-amidinourea
1-(3'-methyltetrahydrofurfuryl)-3-amidinourea
1-(1'-imidazolylmethyl)-3-amidinourea
1-(2'-methyl-1'-imidazolylmethyl)-3-amidinourea
1-[2-(3'-pyridyl)ethyl]-3-(N,N—pentamethyleneamidino)urea
1-[2-(4'-pyridyl)ethyl]-3-(N,N—dimethylamidino)urea
1-[2-(4'-pyridyl)ethyl]-3-(N,N—diethylamidino)urea
1-[2-(4'-pyridyl)ethyl]-3-(N—methyl-N—ethylamidino)urea
1-[2-(3'-methyl-2'-pyridyl)ethyl]-3-(N,N—tetramethyleneamidino)urea
1-[2-(3'-methyl-2'-pyridyl)ethyl]-3-(N,N—pentamethyleneamidino)urea
1-(2'-methyl-3'-pyridylmethyl)-3-(methylamidino)urea
1-(2'-ethyl-3'-pyridylmethyl)-3-(methylamidino)urea
1-(2',6'-dimethyl-3'-pyridylmethyl)-3-(methylamidino)urea
1-(3'-cyano-2'-thiophenylmethyl)-3-(methylamidino)urea
1-(3'-carbomethoxy-2'-thiophenylmethyl)-3-(methylamidino)urea
1-(3'-carboethoxy-2'-thiophenylmethyl)-3-(methylamidino)urea
1-(2'-methoxy-3'-pyridylmethyl)-3-(methylamidino)urea
1-(2'-ethoxy-3'-pyridylmethyl)-3-(methylamidino)urea
1-(2'-chloro-3'-pyridylmethyl)-3-(methylamidino)urea
1-furfuryl-3-amidinourea
1-(3'-methyl-furfuryl)-3-amidinourea
1-furfuryl-3-ethylamidinourea
1-furfuryl-3-propylamidinourea
1-furfuryl-3-i-propylamidinourea
1-furfuryl-3-butylamidinourea
1-furfuryl-3-i-butylamidinourea
1-furfuryl-3-sec-butylamidinourea
1-furfuryl-3-t-butylamidinourea
1-furfuryl-3-pentylamidinourea
1-furfuryl-3-hexylamidinourea
1-furfuryl-3-heptylamidinourea
1-furfuryl-3-cyclopropylamidinourea
1-furfuryl-3-cyclobutylamidinourea
1-(2'-pyridylmethyl-N—oxide)-3-methylamidinourea
1-(3'-pyridylmethyl-N—oxide)-3-methylamidinourea
1-(4'-pyridylmethyl-N—oxide)-3-methylamidinourea
1-furfuryl-3-methylamidinourea
1-tetrahydrofurfuryl-3-methylamidinourea
1-[2-(3'-chloro-2'-pyridyl)ethyl]-3-methylamidinourea
1-[2-(3'-chloro-2'-pyridyl)ethyl]-3-ethylamidinourea
1-[2-(3'-chloro-2'-pyridyl)ethyl]-3-propylamidinourea
1-[2-(3'-chloro-2'-pyridyl)ethyl]-3-i-propylamidinourea
1-[2-(3'-chloro-2'-pyridyl)ethyl]-3-butylamidinourea
1-[2-(3'-chloro-2'-pyridyl)ethyl]-3-i-butylamidinourea
1-[2-(3'-chloro-2'-pyridyl)ethyl]-3-t-butylamidinourea
1-[2-(3'-chloro-2'-pyridyl)ethyl]-3-pentylamidinourea
1-[2-(3'-chloro-2'-pyridyl)ethyl]-3-allylamidinourea
1-[2-(3'-chloro-2'-pyridyl)ethyl]-3-propargylamidinourea
1-[2-(2'-pyridyl)ethyl]-3-methylamidinourea
1-[2-(2'-pyridyl)ethyl]-3-ethylamidinourea
1-[2-(2'-pyridyl)ethyl]-3-propylamidinourea
1-[2-(2'-pyridyl)ethyl]-3-i-propylamidinourea
1-[2-(2'-pyridyl)ethyl]-3-butylamidinourea
1-[2-(2'-pyridyl)ethyl]-3-i-butylamidinourea
1-(4'-pyridylmethyl)-3-(N,N—dimethylamidino)urea
1-(4'-pyridylmethyl)-3-(N,N—diethylamidino)urea
1-(4'-pyridylmethyl)-3-(N—methyl-N—ethylamidino)urea
1-[2-(3'-methyl-2'-pyridyl)ethyl]-3-cyclopropylamidinourea
1-[2-(3'-methyl-2'-pyridyl)ethyl]-3-methoxyethylamidinourea
1-[2-(3'-methyl-2'-pyridyl)ethyl]-3-benzyloxyethylamidinourea
1-[2-(3'-methyl-2'-pyridyl)ethyl]-3-phenethoxyethylamidinourea
1-[2-(3'-methyl-2'-pyridyl)ethyl]-3-benzylamidinourea
1-[2-(3'-methyl-2'-pyridyl)ethyl]-3-(N,N—dimethylamidino)urea
1-[2-(3'-methyl2'-pyridyl)ethyl]-3-(N,N—diethylamidino)urea
1-(3'-methyl-2'-pyridylmethyl)-3-phenethoxyethylamidinourea
1-(3'-methyl-2'-pyridylmethyl)-3-benzylamidinourea TABLE I-continued 1-(3'-methyl-2'-pyridylmethyl)-3-(N,N—dimethylamidino)urea
1-(3'-methyl-2'-pyridylmethyl)-3-(N,N—diethylamidino)urea
1-(3'-methyl-2'-pyridylmethyl)-3-(N,N—tetramethyleneamidino)urea
1-(3'-methyl-2'-pyridylmethyl)-3-(N,N—pentamethyleneamidino)urea
1-(2'-methyl,6'-chloro-4'-pyridylmethyl)-3-methylamidinourea
1-(3'-chloro-2'-pyridylmethyl)-3-(N—[3'-cyclopentenyl]-amidino)urea
1-(3'-chloro-2'-pyridylmethyl)-3-cyclopropylmethylamidinourea
1-(3'-chloro-2'-pyridylmethyl)-3-methoxyethylamidinourea
1-(3'-chloro-2'-pyridylmethyl)-3-benzyloxyethylamidinourea
1-(3'-chloro-2'-pyridylmethyl)-3-phenethoxyethylamidinourea
1-(3'-chloro-2'-pyridylmethyl)-3-benzylamidinourea
1-(3'-chloro-2'-pyridylmethyl)-3-(N,N—dimethylamidino)urea
1-(3'-chloro-2'-pyridylmethyl)-3-(N,N—diethylamidino)urea
1-(3'-chloro-2'-pyridylmethyl)-3-(N,N—tetramethyleneamidino)urea
1-(2'-pyridylmethyl)-3-(N,N[3'-methyl-3'-azapentamethylene]amidino)urea
1-(2'-pyridylmethyl-3-(N,N[3'-oxapentamethylene]amidino)urea
1-(2'-ethyl-4'-pyridylmethyl)-3-(N,N—tetramethyleneamidino)urea
1-(3'-chloro-2'-pyridylmethyl)-3-methylamidinourea
1-(3'-chloro-2'-pyridylmethyl)-3-ethylamidinourea
1-(3'-chloro-2'-pyridylmethyl)-3-propylamidinourea
1-(3'-chloro-2'-pyridylmethyl)-3-i-propylamidinourea
1-(3'-chloro-2'-pyridylmethyl)-3-butylamidinourea
1-(3'-chloro-2'-pyridylmethyl)-3-i-butylamidinourea
1-(3'-chloro-2'-pyridylmethyl)-3-t-butylamidinourea
1-(3'-chloro-2'-pyridylmethyl)-3-pentylamidinourea
1-(3'-chloro-2'-pyridylmethyl)-3-allylamidinourea
1-(3'-chloro-2'-pyridylmethyl)-3-propargylamidinourea
1-(3'-chloro-2'-pyridylmethyl)-3-cyclopropylamidinourea
1-(3'-chloro-2'-pyridylmethyl)-3-cyclobutylamidinourea
1-(3'-pyridylmethyl)-3-methylamidinourea
1-(3'-pyridylmethyl)-3-ethylamidinourea
1-(3'-pyridylmethyl)-3-propylamidinourea
1-(3'-pyridylmethyl)-3-i-propylamidinourea
1-(3'-pyridylmethyl)-3-butylamidinourea
1-(3'-pyridylmethyl)-3-i-butylamidinourea
1-[2-(3'-chloro-2'-pyridyl)ethyl]-3-cyclopropylamidinourea
1-[2-(3'-chloro-2'-pyridyl)ethyl]-3-cyclobutylamidinourea
1-[2-(3'-chloro-2'-pyridyl)ethyl]-3-(N—]3'-cyclopentenyl]-amidino)urea
1-[2-(3'-chloro-2'-pyridyl)ethyl]-3-cyclopropylmethylamidinourea
1-[2-(3'-chloro-2'-pyridyl)ethyl]-3-methoxyethylamidinourea
1-[2-(3'-chloro-2'-pyridyl)ethyl]-3-benzyloxyethylamidinourea
1-[2-(3'-chloro-2'-pyridyl)ethyl]-3-phenethoxyethylamidinourea
1-[2-(3'-chloro-2'-pyridyl)ethyl]-3-benzylamidinourea
1-[2-(3'-chloro-2'-pyridyl)ethyl]-3-(N,N—dimethylamidino)urea
1-[2-(3'-chloro-2'-pyridyl)ethyl]-3-(N,N—dimethylamidino)urea
1-[2-(3'-chloro-2'-pyridyl)ethyl]-3-(N,N—diethylamidino)urea
1-[2-(3'-chloro-2'-pyridyl)ethyl]-3-(N,N—tetramethyleneamidino)urea
1-[2-(2'-pyridyl)ethyl]-3-(N,N[3'-methyl-3'-azapentamethylene]amidino)urea
1-[2-(2'-pyridyl)ethyl]-3-(N,N[3'-oxapentamethylene]amidino)urea
1-[3-(3'-methyl-2'-pyridyl)propyl]-3-cyclopropylamidinourea
1-[3-(3'-methyl-2'-pyridyl)propyl]-3-methoxyethylamidinourea
1-[3-(3'-methyl-2'-pyridyl)propyl]-3-benzyloxyethylamidinourea
1-[3-(3'-methyl-2' -pyridyl)propyl]-3-phenethoxyethylamidinourea
1-[3-(3'-methyl-2'-pyridyl)propyl]-3-benzylamidinourea
1-[3-(3'-methyl-2'-pyridyl)propyl]-3-(N,N—dimethylamidino)urea
1-[3-(3'-methyl-2'-pyridyl)propyl]-3-(N,N—diethylamidino)urea
1-[3-(3'-chloro-2'-pyridyl)propyl]-3-cyclopropylamidinourea
1-[3-(3'-chloro-2'-pyridyl)propyl]-3-cyclobutylamidinourea TABLE I-continued 1-[3-(3'-chloro-2'-pyridyl)propyl]-3-(N—[3'-cyclopentenyl]-amidino)urea
1-[3-(3'-chloro-2'-pyridyl)propyl]-3-cyclopropylmethylamidinourea
1-[3-(3'-chloro-2'-pyridyl)propyl]-3-methoxyethylamidinourea
1-[3-(3'-chloro-2'-pyridyl)propyl]-3-benzyloxyethylamidinourea
1-[3-(3'-chloro-2'-pyridyl)propyl]-3-phenethoxyethylamidinourea
1-[3-(3'-chloro-2'-pyridyl)propyl]-3-benzylamidinourea
1-[3-(3'-chloro-2'-pyridyl)propyl]-3-(N,N—dimethylamidino)urea
1-[3-(3'-chloro-2'-pyridyl)propyl]-3-(N,N—diethylamidino)urea
1-[3-(3'-chloro-2'-pyridyl)propyl]-3-(N,N—tetramethyleneamidino)urea
1-[3-(2'-pyridyl)propyl]-3-(N,N[3'-methyl-3'-azapentamethylene]amidino)urea
1-[3-(2'-pyridyl)propyl]-3-(N,N[3'-oxapentamethylene]amidino)urea
1-[3-(3'-chloro-2'-pyridyl)propyl]-3-(N—[3'-cyclopentenyl]-amidinourea
1-[3-(3'-chloro-2'-pyridyl)propyl]-3-cyclopropylmethylamidinourea
1-[3-(3'-chloro-2'-pyridyl)propyl]-3-methoxyethylamidinourea
1-[3-(3'-chloro-2'-pyridyl)propyl]-3-benzyloxyethylamidinourea
1-[3-(3'-chloro-2'-pyridyl)propyl]-3-phenethoxyethylamidinourea
1-[3-(3'-chloro-2'-pyridyl)propyl]-3-benzylamidinourea
1-[3-(3'-chloro-2'-pyridyl)propyl]-3-(N,N—dimethylamidino)urea
1-[3-(3'-chloro-2'-pyridyl)propyl]-3-(N,N—diethylamidino)urea
1-[3-(3'-chloro-2'-pyridyl)propyl]-3-(N,N—tetramethyleneamidino)urea
1-[3-(2'-pyridyl)propyl]-3-(N,N[3'-methyl-3'-azapentamethylene]amidino)urea
1-[3-(2'-pyridyl)propyl]-3-(N,N[3'-oxapentamethylene]amidino)urea
1-[3-(3'-methyl-2'-pyridyl)propyl]-3-(N,N—tetramethyleneamidino)urea
1-[3-(3'-methyl-2'-pyridyl)propyl]-3-(N,N—pentamethyleneamidino)urea
1-[3-(4'-pyridyl)propyl]-3-(N—methyl-N—ethylamidino)urea
1-[3-(4'-pyridyl)propyl]-3-(N,N—dimethylamidino)urea
1-[3-(4'-pyridyl)propyl]-3-(N,N—diethylamidino)urea
1-[3-(4'-pyridyl)propyl]-3-(N,N—pentamethyleneamidino)urea
1-[3-(3'-chloro-2'-pyridyl)propyl]-3-methylamidinourea
1-[3-(3'-chloro-2'-pyridyl)propyl]-3-ethylamidinourea
1-[3-(3'-chloro-2'-pyridyl)propyl]-3-propylamidinourea
1-[3-(3'-chloro-2'-pyridyl)propyl]-3-i-propylamidinourea
1-[3-(3'-chloro-2'-pyridyl)propyl]-3-butylamidinourea
1-[3-(3'-chloro-2'-pyridyl)propyl]-3-i-butylamidinourea
1-[3-(3'-chloro-2'-pyridyl)propyl]-3-t-butylamidinourea
1-[3-(3'-chloro-2'-pyridyl)propyl]-3-pentylamidinourea
1-[3-(3'-chloro-2'-pyridyl)propyl]-3-allylamidinourea
1-[3-(3'-chloro-2'-pyridyl)propyl]-3-propargylamidinourea
1-[3-(3'-chloro-2'-pyridyl)propyl]-3-cyclopropylamidinourea
1-[3-(3'-chloro-2'-pyridyl)propyl]-3-cyclobutylamidinourea
1-[3-(3'-chloro-2'-pyridyl)propyl]-3-methylamidinourea
1-[3-(3'-chloro-2'-pyridyl)propyl]-3-ethylamidinourea
1-[3-(3'-chloro-2'-pyridyl)propyl]-3-propylamidinourea
1-[3-(3'-chloro-2'-pyridyl)propyl]-3-i-propylamidinourea
1-[3-(3'-chloro-2'-pyridyl)propyl]-3-butylamidinourea
1-[3-(3'-chloro-2' -pyridyl)propyl]-3-i-butylamidinourea
1-[3-(3'-chloro-2'-pyridyl)propyl]-3-t-butylamidinourea
1-[3-(3'-chloro-2'-pyridyl)propyl]-3-pentylamidinourea
1-[3-(3'-chloro-2'-pyridyl)propyl]-3-allylamidinourea
1-[3-(3'-chloro-2'-pyridyl)propyl]-3-propargylamidinourea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea
1-[3-(2'-pyridyl)propyl]-3-butylamidinourea
1-[3-(2'-pyridyl)propyl]-3-i-butylamidinourea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea TABLE I-continued 1-[3-(2'-pyridyl)propyl]-3-butylamidinourea
1-[3-(2'-pyridyl)propyl]-3-i-butylamidinourea
1-(2'-pyridylmethyl)-3-methylamidinothiourea
1-(2'-pyridylmethyl)-3-ethylamidinothiourea
1-(2'-pyridylmethyl)-3-propylamidinothiourea
1-(2'-pyridylmethyl)-3-i-propylamidinothiourea
1-(2'-pyridylmethyl)-3-butylamidinothiourea
1-(2'-pyridylmethyl)-3-i-butylamidinothiourea
1-(2'-pyridylmethyl)-3-pentylamidinothiourea
1-(2'-pyridylmethyl)-3-propargylamidinothiourea
1-(2'-pyridylmethyl)-3-allylamidinothiourea
1-(2'-pyridylmethyl)-3-methoxyethylamidinothiourea
1-(2'-pyridylmethyl)-3-benzyloxyethylamidinothiourea
1-(2'-pyridylmethyl)-3-phenethoxyethylamidinothiourea
1-(2'-pyridylmethyl)-3-(N,N—dimethylamidino)thiourea
1-(3'-methyl-2'-pyridylmethyl)-3-methylamidinothiourea
1-(3'-methyl-2'-pyridylmethyl)-3-ethylamidinothiourea
1-(3'-methyl-2'-pyridylmethyl)-3-propylamidinothiourea
1-(3'-methyl-2'-pyridylmethyl)-3-i-propylamidinothiourea
1-(3'-methyl-2'-pyridylmethyl)-3-i-butylamidinothiourea
1-(3'-methyl-2'-pyridylmethyl)-3-pentylamidinothiourea
1-(3'-methyl-2'-pyridylmethyl)-3-allylamidinothiourea
1-(3'-methyl-2'-pyridylmethyl)-3-propargylamidinothiourea
1-(3'-methyl-2'-pyridylmethyl)-3-benzylamidinothiourea
1-(3'-chloro-2'-pyridylmethyl)-3-benzylamidinothiourea
1-(3'-chloro-2'-pyridylmethyl)-3-propargylamidinothiourea
1-(3'-chloro-2'-pyridylmethyl)-3-cyclopropylamidinothiourea
1-(3'-chloro-2'-pyridylmethyl)-3-cyclobutylamidinothiourea
1-(3'-chloro-2'-pyridylmethyl)-3-methylamidinothiourea
1-(3'-chloro-2'-pyridylmethyl)-3-ethylamidinothiourea
1-(3'-chloro-2'-pyridylmethyl)-3-propylamidinothiourea
1-(3'-chloro-2'-pyridylmethyl)-3-i-propylamidinothiourea
1-(3'-chloro-2'-pyridylmethyl)-3-butylamidinothiourea
1-(3'-chloro-2'-pyridylmethyl)-3-i-butylamidinothiourea
1-(3'-chloro-2'-pyridylmethyl)-3-t-butylamidinothiourea
1-(3'-chloro-2'-pyridylmethyl)-3-pentylamidinothiourea
1-(3'-chloro-2'-pyridylmethyl)-3-allylamidinothiourea
1-(2'-pyridylmethyl)-3-methylamidinothiourea
1-(2'-pyridylmethyl)-3-ethylamidinothiourea
1-(2'-pyridylmethyl)-3-propylamidinothiourea
1-(2'-pyridylmethyl)-3-i-propylamidinothiourea
1-(2'-pyridylmethyl)-3-butylamidinothiourea
1-(2'-pyridylmethyl)-3-i-butylamidinothiourea
1-(2'-pyridylmethyl)-3-(N,N—diethylamidino)thiourea
1-(2'-pyridylmethyl)-3-(N,N—tetramethyleneamidino)thiourea
1-(2'-pyridylmethyl)-3-(N,N—pentamethyleneamidino)thiourea
1-(2'-pyridylmethyl)-3-(N,N—hexamethyleneamidino)thiourea
1-(4'-pyridylmethyl)-3-(N,N—dimethylamidino)thiourea
1-(4'-pyridylmethyl)-3-(N,N—diethylamidino)thiourea
1-(4'-pyridylmethyl)-3-(N—methyl-N—ethylamidino)thiourea
1-(3'-pyridylmethyl)-3-(N,N—pentamethyleneamidino)thiourea
1-(3'-methyl-2'-pyridylmethyl)-3-(N,N—tetramethyleneamidino)thiourea
1-(3'-methyl-2'-pyridylmethyl)-3-(N,N—pentamethyleneamidino)thiourea
1-(3'-chloro-2'-pyridylmethyl)-3-benzyloxyethylamidinothiourea
1-[2-(2'-pyridyl)ethyl]-3-methylamidinothiourea
1-[2-(2'-pyridyl)ethyl]-3-ethylamidinothiourea
1-[2-(2'-pryidyl)ethyl]-3-propylamidinothiourea
1-[2-(2'-pyridyl)ethyl]-3-i-propylamidinothiourea
1-[2-(2'-pyridyl)ethyl]-3-butylamidinothiourea
1-[2-(2'-pyridyl)ethyl]-3-i-butylamidinothiourea
1-[2-(2'-pyridyl)ethyl]-3-pentylamidinothiourea
1-[2-(2'-pyridyl)ethyl]-3-propargylamidinothiourea
1-[2-(2'-pyridyl)ethyl]-3-allylamidinothiourea
1-[2-(2'-pyridyl)ethyl]-3-methoxyethylamidinothiourea
1-[2-(2'-pyridyl)ethyl]-3-benzyloxyethylamidinothiourea
1-[2-(2'-pyridyl)ethyl]-3-phenethoxyethylamidinothiourea
1-[2-(2'-pyridyl)ethyl]-3-(N,N—dimethylamidino)thiourea
1-[2-(2'-pyridyl)ethyl]-3-(N,N—diethylamidino)thiourea
1-[2-(2'-pyridyl)ethyl]-3-methylamidinothiourea
1-[2-(2'-pyridyl)ethyl]-3-ethylamidinothiourea
1-[2-(2'-pyridyl)ethyl]-3-propylamidinothiourea
1-[2-(2'-pyridyl)ethyl]-3-i-propylamidinothiourea
1-[2-(2'-pyridyl)ethyl]-3-butylamidinothiourea
1-[2-(2'-pyridyl)ethyl]-3-i-butylamidinothiourea
1-[2-(2'-pyridyl)ethyl]-3-(N,N—tetramethyleneamidino)thiourea
1-[2-(2'-pyridyl)ethyl]-3-(N,N—pentamethyleneamidino)thiourea
1-[2-(2'-pyridyl)ethyl]-3-(N,N—hexamethyleneamidino)thiourea
1-[3-(3'-pyridyl)propyl]-3-(N,N—pentamethyleneamidino)thiourea
1-(3'-pyridylmethyl)-3-t-butylamidinothiourea
1-(3'-pyridylmethyl)-3-pentylamidinothiourea
1-(3'-pyridylmethyl)-3-allylamidinothiourea
1-(3'-pyridylmethyl)-3-propargylamidinothiourea
1-(3'-pyridylmethyl)-3-cyclobutylamidinothiourea
1-(3'-pyridylmethyl)-3-cyclohexylamidinothiourea
1-(3'-pyridylmethyl)-3-benzylamidinothiourea
1-(3'-pyridylmethyl)-3-methoxyethylamidinothiourea
1-(3'-pyridylmethyl)-3-benzyloxyethylamidinothiourea
1-(3'-pyridylmethyl)-3-methoxyethylamidinothiourea
1-(3'-pyridylmethyl)-3-benzyloxyethylamidinothiourea
1-(3'-pyridylmethyl)-3-phenethoxyethylamidinothiourea
1-(3'-pyridylmethyl)-3-(N,N—dimethylamidino)thiourea
1-(3'-pyridylmethyl)-3-(N,N—diethylamidino)thiourea
1-(4'-pyridylmethyl)-3-methylamidinothiourea
1-(4'-pyridylmethyl)-3-ethylamidinothiourea
1-(4'-pyridylmethyl)-3-propylamidinothiourea
1-(4'-pyridylmethyl)-3-i-propylamidinothiourea
1-(4'-pyridylmethyl)-3-butylamidinothiourea
1-(4'-pyridylmethyl)-3-t-butylamidinothiourea
1-(4'-pyridylmethyl)-3-pentylamidinothiourea
1-(4'-pyridylmethyl)-3-hexylamidinothiourea
1-(4'-pyridylmethyl)-3-propargylamidinothiourea
1-(4'-pyridylmethyl)-3-allylamidinothiourea
1-(4'-pyridylmethyl)-3-methoxyethylamidinothiourea
1-(4'-pyridylmethyl)-3-benzyloxyethylamidinothiourea
1-(4'-pyridylmethyl)-3-phenethoxyethylamidinothiourea
1-[2-(3'-pyridyl)ethyl]-3-t-butylamidinothiourea
1-[2-(3'-pyridyl)ethyl]-3-pentylamidinothiourea
1-[2-(3'-pyridyl)ethyl]-3-allylamidinothiourea
1-[2-(3'-pyridyl)ethyl]-3-propargylamidinothiourea
1-[2-(3'-pyridyl)ethyl]-3-cyclobutylamidinothiourea
1-[2-(3'-pyridyl)ethyl]-3-cyclohexylamidinothiourea
1-[2-(3'-pyridyl)ethyl]-3-benzylamidinothiourea
1-[2-(3'-pyridyl)ethyl]-3-methoxyethylamidinothiourea
1-[2-(3'-pyridyl)ethyl]-3-benzyloxyethylamidinothiourea
1-[2-(3'-pyridyl)ethyl]-3-methoxyethylamidinothiourea
1-[2-(3'-pyridyl)ethyl]-3-benzyloxyethylamidinothiourea
1-[2-(3'-pyridyl)ethyl]-3-phenethoxyethylamidinothiourea
1-[2-(3'-pyridyl)ethyl]-3-(N,N—dimethylamidino)thiourea
1-[2-(3'-pyridyl)ethyl]-3-(N,N— diethylamidino)thiourea
1-[2-(4'-pyridyl)ethyl]-3-methylamidinothiourea
1-[2-(4'-pyridyl)ethyl]-3-ethylamidinothiourea
1-[2-(4'-pyridyl)ethyl]-3-propylamidinothiourea
1-[2-(4'-pyridyl)ethyl]-3-i-propylamidinothiourea
1-[2-(4'-pyridyl)ethyl]-3-butylamidinothiourea
1-[2-(4'-pyridyl)ethyl]-3-t-butylamidinothiourea
1-[2-(4'-pyridyl)etthyl]-3-pentylamidinothiourea
1-[2-(4'-pyridyl)ethyl]-3-hexylamidinothiourea
1-[2-(4'-pyridyl)ethyl]-3-propargylamidinothiourea
1-[2-(4'-pyridyl)ethyl]-3-allylamidinothiourea
1-[2-(4'-pyridyl)ethyl]-3-methoxyethylamidinothiourea
1-[3-(2'-pyridyl)propyl]-3-methylamidinothiourea
1-[3-(2'-pyridyl)propyl]-3-ethylamidinothiourea
1-[3-(2'-pyridyl)propyl]-3-propylamidinothiourea
1-[3-(2'-pyridyl)propyl]-3-i-propylamidinothiourea
1-[3-(2'-pyridyl)propyl]-3-butylamidinothiourea
1-[3-(2'-pyridyl)propyl]-3-i-butylamidinothiourea
1-[3-(2'-pyridyl)propyl]-3-methoxyethylamidinothiourea
1-[3-(2'-pyridyl)propyl]-3-benzyloxyethylamidinothiourea
1-[3-(2'-pyridyl)propyl]-3-phenethoxyethylamidinothiourea
1-[3-(2'-pyridyl)propyl]-3-(N,N—dimethylamidino)thiourea
1-[3-(2'-pyridyl)propyl]-3-(N,N—diethylamidino)thiourea
1-[3-(2'-pyridyl)propyl]-3-methylamidinothiourea
1-[3-(2'-pyridyl)propyl]-3-ethylamidinothiourea
1-[3-(2'-pyridyl)propyl]-3-propylamidinothiourea
1-[3-(2'-pyridyl)propyl]-3-i-propylamidinothiourea
1-[3-(2'-pyridyl)propyl]-3-butylamidinothiourea
1-[3-(2'-pyridyl)propyl]-3-i-butylamidinothiourea
1-[3-(2'-pyridyl)propyl]-3-pentylamidinothiourea
1-[3-(2'-pyridyl)propyl]-3-propargylamidinothiourea
1-[3-(2'-pyridyl)propyl]-3-allylamidinothiourea
1-[3-(4'-pyridyl)propyl]-3-methylamidinothiourea
1-[3-(4'-pyridyl)propyl]-3-ethylamidinothiourea
1-[3-(4'-pyridyl)propyl]-3-propylamidinothiourea
1-[3-(4'-pyridyl)propyl]-3-i-propylamidinothiourea
1-[3-(4'-pyridyl)propyl]-3-butylamidinothiourea
1-[2-(3'-methyl-2'-pyridyl)ethyl]-3-(N,N—tetramethyleneamidino)thiourea

TABLE I-continued

1-[2-(3'-methyl-2'-pyridyl)ethyl]-3-(N,N—pentamethyleneamidino)thiourea
1-[3-(4'-pyridyl)propyl]-3-t-butylamidinothiourea
1-[3-(4'-pyridyl)propyl]-3-pentylamidinothiourea
1-[3-(4'-pyridyl)propyl]-3-hexylamidinothiourea
1-[3-(4'-pyridyl)propyl]-3-propargylamidinothiourea
1-[3-(4'-pyridyl)propyl]-3-allylamidinothiourea
1-[3-(4'-pyridyl)propyl]-3-methoxyethylamidinothiourea
1-[3-(4'-pyridyl)propyl]-3-benzyloxyethylamidinothiourea
1-[3-(4'-pyridyl)propyl]-3-phenethoxyethylamidinothiourea
1-[3-(4'-pyridyl)propyl]-3-(N,N—dimethylamidino)thiourea
1-[3-(4'-pyridyl)propyl]-3-(N,N—diethylamidino)thiourea
1-[3-(4'-pyridyl)propyl]-3-(N—methyl-N—ethylamidino)thiourea
1-[3-(3'-chloro-2'-pyridyl)propyl]-3-methylamidinothiourea
1-[3-(3'-chloro-2'-pyridyl)propyl]-3-ethylamidinothiourea
1-[3-(3'-chloro-2'-pyridyl)propyl]-3-propylamidinothiourea
1-[3-(3'-chloro-2'-pyridyl)propyl]-3-i-propylamidinothiourea
1-[3-(3'-chloro-2'-pyridyl)propyl]-3-butylamidinothiourea
1-[3-(3'-chloro-2'-pyridyl)propyl]-3-i-butylamidinothiourea
1-[3-(3'-chloro-2'-pyridyl)propyl]-3-t-butylamidinothiourea
1-[3-(3'-chloro-2'-pyridyl)propyl]-3-pentylamidinothiourea
1-[3-(3'-chloro-2'-pyridyl)propyl]-3-allylamidinothiourea
1-[3-(3'-pyridyl)propyl]-3-t-butylamidinothiourea
1-[3-(3'-pyridyl)propyl]-3-pentylamidinothiourea
1-[3-(3'-pyridyl)propyl]-3-allylamidinothiourea
1-[3-(3'-pyridyl)propyl]-3-propargylamidinothiourea
1-[3-(3'-pyridyl)propyl]-3-cyclobutylamidinothiourea
1-[3-(3'-pyridyl)propyl]-3-cyclohexylamidinothiourea
1-[3-(3'-pyridyl)propyl]-3-benzylamidinothiourea
1-[3-(3'-pyridyl)propyl]-3-methoxyethylamidinothiourea
1-[3-(3'-pyridyl)propyl]-3-benzyloxyethylamidinothiourea
1-[3-(3'-pyridyl)propyl]-3-methoxyethylamidinothiourea
1-[3-(3'-pyridyl)propyl]-3-benzyloxyethylamidinothiourea
1-[3-(3'-pyridyl)propyl]-3-phenethoxyethylamidinothiourea
1-[3-(3'-pyridyl)propyl]-3-(N,N—dimethylamidino)thiourea
1-[3-(3'-pyridyl)propyl]-3-(N,N—diethylamidino)thiourea

TABLE 1-A $$R_1-NH-\overset{X}{\overset{\|}{C}}-NH-\overset{NH}{\overset{\|}{C}}-N\overset{R_5}{\underset{R_6}{}}$$

X may be oxygen or sulfur

| $R_1$ | $R_5$ | $R_6$ |
|---|---|---|
| 2,3-dimethyl-4-methyl-pyridyl (4-CH₃, 3-CH₃, 2-CH₃) | H | H |
| 2,3-dimethyl-4-methyl-pyridyl | H | —CH₃ |
| 2,3-dimethyl-4-methyl-pyridyl | H | —C₂H₅ |
| 2,3-dimethyl-4-methyl-pyridyl | H | —OCH₃ |
| 2,3-dimethyl-4-methyl-pyridyl | —CH₃ | —CH₃ |
| 2,3-dimethyl-4-methyl-pyridyl | —CH₃ | —C₂H₅ |
| 3-ethyl-2-pyridyl N-oxide | H | H |
| 2-pyridyl | H | H |
| 2-pyridyl | H | —CH₃ |
| 2-pyridyl N-oxide | H | —C₂H₅ |
| 2-pyridyl | —CH₃ | —CH₃ |
| 3-pyridyl | H | —OCH₃ |

TABLE 1-A-continued

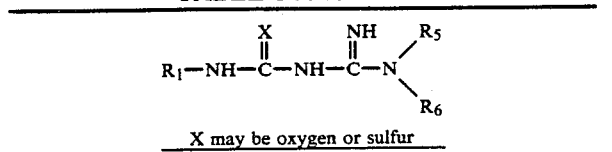

X may be oxygen or sulfur

| R₁ | R₅ | R₆ |
|---|---|---|
| 3-methyl-2-pyridinyl | H | —CH₃ |
| 2-furyl | H | —CH₃ |
| 2-furyl | H | H |
| 3-furyl | H | —CH₃ |
| 3-furyl | H | —C₂H₅ |
| 2-thienyl | H | —CH₃ |
| 2-thienyl | —CH₃ | —CH₃ |
| 1-methyl-2-pyrrolyl | —H | —CH₃ |
| 1-methyl-2-pyrrolyl | —H | —C₂H₅ |
| 5-isoxazolyl | —H | —CH₃ |
| 3,5-dichloro-4-pyridinyl | H | —CH₃ |
| 3,5-dichloro-4-pyridinyl | H | —C₂H₅ |
| 3-chloro-2-thienyl | H | —CH₃ |
| 3-chloro-2-thienyl | H | —C₂H₅ |
| 3,5-dimethyl-2-thienyl | H | —CH₃ |
| 3,5-dimethyl-2-thienyl | H | —C₂H₅ |
| 3-methyl-5-chloro-2-thienyl | H | —CH₃ |
| 3-methyl-5-chloro-2-thienyl | H | —C₂H₅ |
| 3-methyl-5-chloro-2-thienyl | H | —CH₃ |
| 4,6-dimethyl-5-pyrimidinyl | —CH₃ | —CH₃ |

TABLE 1-A-continued
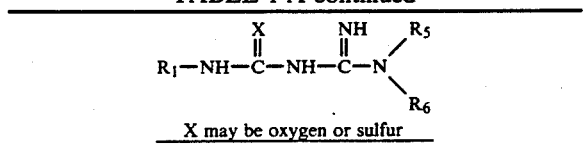
X may be oxygen or sulfur

TABLE 1-A-continued $$R_1-NH-\overset{X}{\underset{}{C}}-NH-\overset{NH}{\underset{}{C}}-N\overset{R_5}{\underset{R_6}{}}$$

X may be oxygen or sulfur

| $R_1$ | $R_5$ | $R_6$ |
|---|---|---|
| pyrimidin-2-yl | —CH$_3$ | —CH$_3$ |
| 4,6-dimethylpyrimidin-2-yl | H | H |
| 4,6-dimethylpyrimidin-2-yl | H | —CH$_3$ |

TABLE 2

| $R_a$ | $R_5$ | $R_6$ |
|---|---|---|
| 3,5-dichloro-4-pyridyl | H | —CH$_3$ |
| 3,5-dichloro-4-pyridyl | H | —C$_2$H$_5$ |
| 3-chloro-2-thienyl | H | —CH$_3$ |
| 3-chloro-2-thienyl | H | —C$_2$H$_5$ |
| 3,4-dimethyl-2-thienyl | H | —CH$_3$ |
| 3,4-dimethyl-2-thienyl | H | —C$_2$H$_5$ |
| 5-chloro-3,4-dimethyl-2-thienyl | H | —CH$_3$ |
| 4,6-dimethylpyrimidin-2-yl | —CH$_3$ | —CH$_3$ |
| 4,6-dimethylpyrimidin-2-yl | H | —C$_2$H$_5$ |
| 4-pyridyl | H | H |
| 4-pyridyl | H | —CH$_3$ |
| 1H-imidazol-2-yl | H | H |
| 1H-imidazol-2-yl | H | —CH$_3$ |
| 1H-imidazol-2-yl | H | —C$_2$H$_5$ |
| 1H-imidazol-2-yl (isomer) | H | H |

TABLE 2-continued

| $R_a$ | $R_5$ | $R_6$ |
|---|---|---|
| 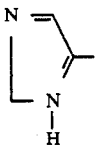 (imidazole) | H | —CH₃ |
|  (2H-pyran) | H | —CH₃ |
| 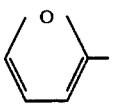 (2H-pyran) | H | H |
| 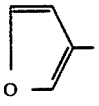 (furan) | H | —CH₃ |
| 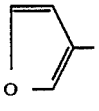 (furan) | H | —C₂H₅ |
| 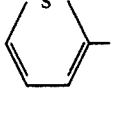 (thiophene) | H | —CH₃ |
| 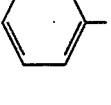 (thiophene) | —CH₃ | —CH₃ |
| 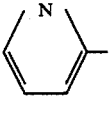 (N-methylpyridine) | —H | —CH₃ |
| 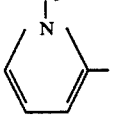 (N-methylpyridine) | —H | —C₂H₅ |
| 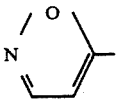 (oxazine) | —H | —CH₃ |
| 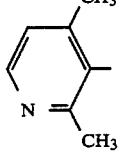 (2,3-dimethyl-4-pyridyl) | H | H |
| 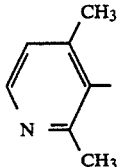 (2,3-dimethyl-4-pyridyl with 4-CH₃) | H | —CH₃ |
| 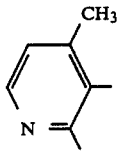 (2,3-dimethyl-4-pyridyl with 4-CH₃) | H | —C₂H₅ |
| 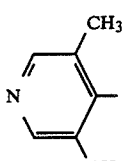 (2,3-dimethyl-4-pyridyl with 4-CH₃) | H | —OCH₃ |
| 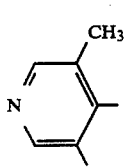 (3,5-dimethyl-4-pyridyl) | H | —CH₃ |
| 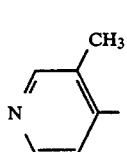 (3,5-dimethyl-4-pyridyl) | —CH₃ | —CH₃ |
| 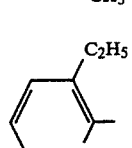 (3,5-dimethyl-4-pyridyl) | —CH₃ | —C₂H₅ |
| 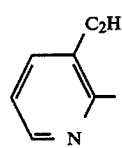 (3-ethyl-2-pyridyl) | H | H |
| 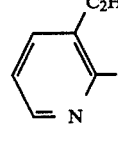 (3-ethyl-2-pyridyl) | H | —CH₃ |
| 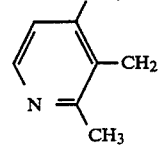 (3-ethyl-2-pyridyl) | H | —C₂H₅ |
| (2,4-dimethyl-3-CH₂-pyridyl) | H | H |

TABLE 2-continued
| $R_a$ | $R_5$ | $R_6$ |
|---|---|---|
| 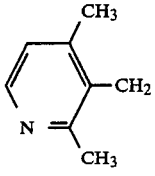 | H | —CH$_3$ |
| 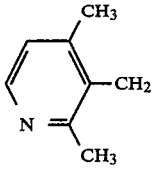 | H | —C$_2$H$_5$ |
| 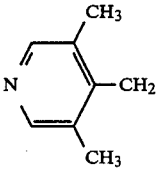 | H | —OCH$_3$ |
| 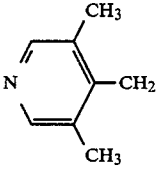 | —CH$_3$ | —CH$_3$ |
| 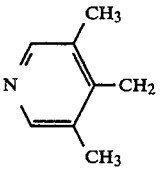 | —CH$_3$ | —C$_2$H$_5$ |
| 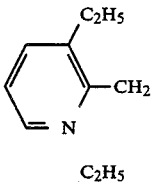 | H | H |
| 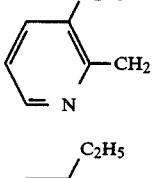 | H | —CH$_3$ |
| 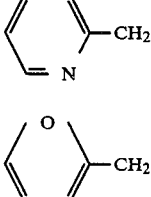 | H | —C$_2$H$_5$ |
| 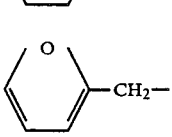 | H | —CH$_3$ |
| 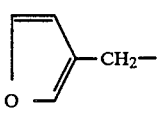 | H | H |
| 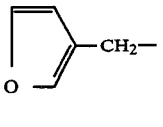 | H | —CH$_3$ |
| 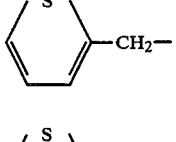 | H | —C$_2$H$_5$ |
| 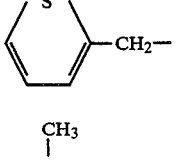 | H | —CH$_3$ |
| 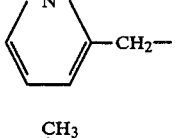 | —CH$_3$ | —CH$_3$ |
| 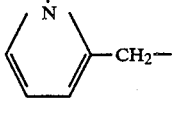 | —H | —CH$_3$ |
| 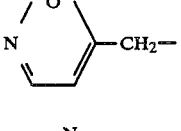 | —H | —C$_2$H$_5$ |
| 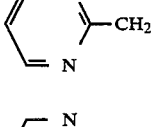 | —H | —CH$_3$ |
| 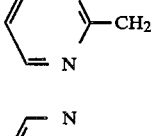 | H | H |
| 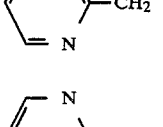 | H | —CH$_3$ |
| 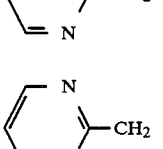 | —CH$_3$ | —CH$_3$ |
| | —H | —CH$_3$ |
| | —H | —C$_2$H$_5$ |

TABLE 2-continued
| $R_a$ | $R_5$ | $R_6$ |
|---|---|---|
| 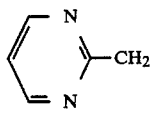 | —CH₃ | —CH₃ |
| 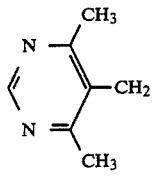 | H | H |
| 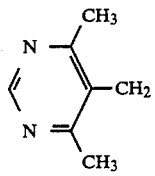 | H | —CH₃ |
| 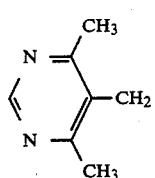 | —CH₃ | —CH₃ |
| 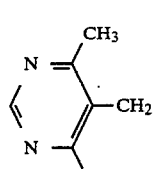 | H | —C₂H₅ |
| 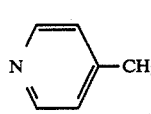 | H | H |
| 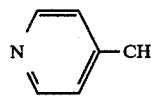 | H | —CH₃ |
| 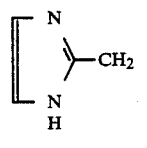 | H | H |
| 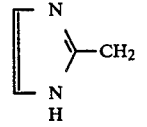 | H | —CH₃ |
| 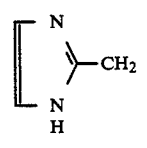 | H | —C₂H₅ |
| 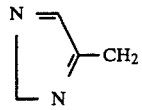 | H | H |
| 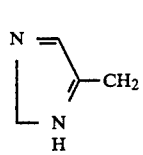 | H | —CH₃ |
| 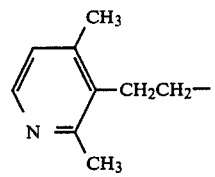 | H | H |
| 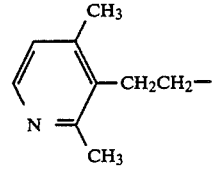 | H | —CH₃ |
| 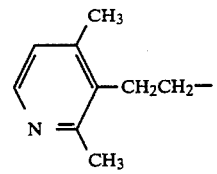 | H | —C₂H₅ |
| 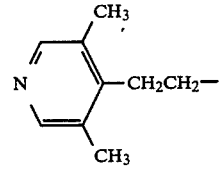 | H | —OCH₃ |
| 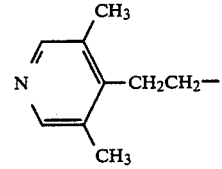 | —CH₃ | —CH₃ |
| 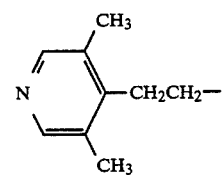 | —CH₃ | —C₂H₅ |
| 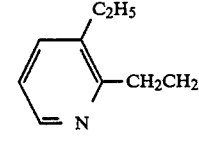 | H | H |

TABLE 2-continued

| $R_a$ | $R_5$ | $R_6$ |
|---|---|---|
| 3-ethyl-pyridin-2-yl-CH₂CH₂– | H | –CH₃ |
| 3-ethyl-pyridin-2-yl-CH₂CH₂– | H | –C₂H₅ |
| pyridin-2-yl-CH₂CH₂– | H | H |
| pyridin-2-yl-CH₂CH₂– | H | –CH₃ |
| pyridin-2-yl-CH₂CH₂– | H | –C₂H₅ |
| pyridin-2-yl-CH₂CH₂– | –CH₃ | –CH₃ |
| pyridin-2-yl-CH₂CH₂– | H | –OCH₃ |
| 3-methyl-pyridin-2-yl-CH₂CH₂– | H | –CH₃ |
| 3-methyl-pyridin-2-yl-CH₂CH₂– | –CH₃ | –CH₃ |
| 3-methyl-pyridin-2-yl-CH₂CH₂– | –C₂H₅ | –C₂H₅ |
| 4,6-dimethyl-pyrimidin-5-yl-CH₂CH₂– | –CH₃ | –CH₃ |
| 4,6-dimethyl-pyrimidin-5-yl-CH₂CH₂– (with ethyl) | H | –C₂H₅ |
| pyridin-4-yl-CH₂CH₂– | H | H |
| pyridin-4-yl-CH₂CH₂– | H | –CH₃ |
| imidazol-2-yl-CH₂CH₂– | H | H |
| imidazol-2-yl-CH₂CH₂– | H | –CH₃ |
| imidazol-2-yl-CH₂CH₂– | H | –C₂H₅ |
| imidazol-4-yl-CH₂CH₂– | H | H |
| imidazol-4-yl-CH₂CH₂– | H | –CH₃ |
| pyrimidin-2-yl-CH₂CH₂– | H | H |
| pyrimidin-2-yl-CH₂CH₂– | H | –CH₃ |
| pyrimidin-2-yl-CH₂CH₂– | –CH₃ | –CH₃ |

TABLE 2-continued

| $R_a$ | $R_5$ | $R_6$ |
|---|---|---|
| pyrimidin-2-yl-CH₂CH₂– | –H | –CH₃ |
| pyrimidin-2-yl-CH₂CH₂– | –H | –C₂H₅ |
| pyrimidin-2-yl-CH₂CH₂– | –CH₃ | –CH₃ |
| 4,6-dimethylpyrimidin-5-yl-CH₂CH₂– | H | H |
| 4,6-dimethylpyrimidin-5-yl-CH₂CH₂– | H | –CH₃ |
| 2H-pyran-3-yl-CH₂–CH₂– | H | –CH₃ |
| 2H-pyran-3-yl-CH₂–CH₂– | H | H |
| furan-3-yl-CH₂–CH₂– | H | –CH₃ |
| furan-3-yl-CH₂–CH₂– | H | –C₂H₅ |
| thiopyran-3-yl-CH₂–CH₂– | H | –CH₃ |
| thiopyran-3-yl-CH₂–CH₂– | –CH₃ | –CH₃ |
| 1-methyl-pyridin-2-yl-CH₂–CH₂– | –H | –CH₃ |
| 1-methyl-pyridin-2-yl-CH₂–CH₂– | –H | –C₂H₅ |
| 1,2-oxazin-3-yl-CH₂–CH₂– | –H | –CH₃ |
| pyrimidin-2-yl | H | H |
| pyrimidin-2-yl | H | –CH₃ |
| pyrimidin-2-yl | –CH₃ | –CH₃ |
| pyrimidin-2-yl | –H | –CH₃ |
| pyrimidin-2-yl | –H | –C₂H₅ |
| pyrimidin-2-yl | –CH₃ | –CH₃ |
| 4,6-dimethylpyrimidin-5-yl | H | H |
| 4,6-dimethylpyrimidin-5-yl | H | –CH₃ |
| isothiazol-5-yl | H | –C₂H₅ |
| pyridin-2-yl | H | H |

TABLE 2-continued

| $R_a$ | $R_5$ | $R_6$ |
|---|---|---|
| 2-pyridyl | H | —CH$_3$ |
| 2-pyridyl | H | —C$_2$H$_5$ |
| 2-pyridyl | —CH$_3$ | —CH$_3$ |
| 2-pyridyl | H | —OCH$_3$ |
| 3-methyl-2-pyridyl | H | —CH$_3$ |
| 3-methyl-2-pyridyl | —CH$_3$ | —CH$_3$ |
| 3-methyl-2-pyridyl | —C$_2$H$_5$ | —C$_2$H$_5$ |
| 5-methylisothiazol-3-yl | H | —CH$_3$ |
| (2-pyridyl)CH$_2$ | H | H |
| (2-pyridyl)CH$_2$ | H | —CH$_3$ |
| (2-pyridyl)CH$_2$ | H | —C$_2$H$_5$ |
| (2-pyridyl)CH$_2$ | —CH$_3$ | —CH$_3$ |
| (2-pyridyl)CH$_2$ | H | —OCH$_3$ |
| (3-methyl-2-pyridyl)CH$_2$ | H | —CH$_3$ |
| (3-methyl-2-pyridyl)CH$_2$ | —CH$_3$ | —CH$_3$ |
| (3-methyl-2-pyridyl)CH$_2$ | —C$_2$H$_5$ | —C$_2$H$_5$ |
| (isoxazol-5-yl) | H | —C$_2$H$_5$ |
| (3,5-dichloro-4-pyridyl)CH$_2$ | H | —CH$_3$ |
| (3,5-dichloro-4-pyridyl)CH$_2$ | H | —C$_2$H$_5$ |
| (3-chloro-2-thienyl)CH$_2$ | H | —CH$_3$ |
| (3-chloro-2-thienyl)CH$_2$ | H | —C$_2$H$_5$ |
| (3,5-dimethyl-2-thienyl)CH$_2$ | H | —CH$_3$ |
| (3,5-dimethyl-2-thienyl)CH$_2$ | H | —C$_2$H$_5$ |

TABLE 2-continued
| $R_a$ | $R_5$ | $R_6$ |
|---|---|---|
| 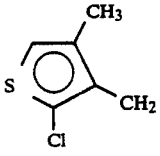 | H | —CH$_3$ |
| 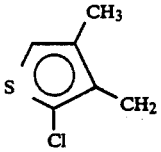 | H | —C$_2$H$_5$ |
| 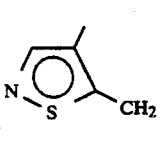 | H | —CH$_3$ |
| 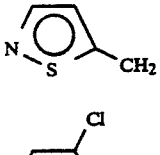 | H | —C$_2$H$_5$ |
| 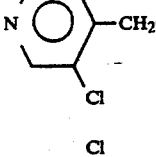 | —CH$_3$ | H |
| 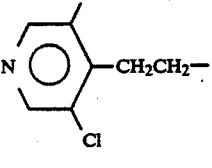 | —C$_2$H$_5$ | H |
| 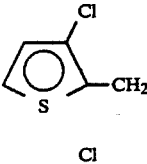 | —CH$_3$ | H |
| 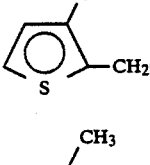 | —C$_2$H$_5$ | H |
| 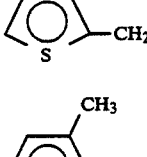 | —CH$_3$ | H |
| 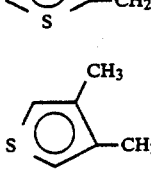 | —C$_2$H$_5$ | H |
|  | —CH$_3$ | H |
| 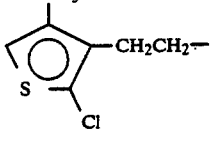 | —C$_2$H$_5$ | H |
| 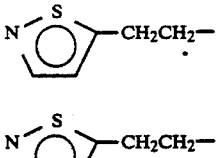 | —CH$_3$ | H |
| 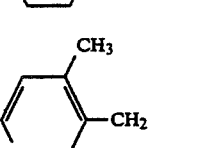 | —C$_2$H$_5$ | H |
| 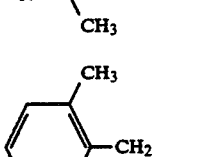 | H | 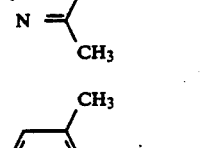 |
| 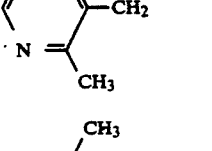 | H | 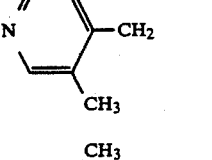 |
| 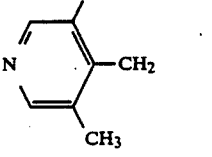 | H | 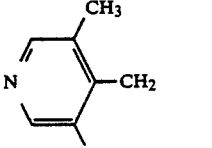 |
| 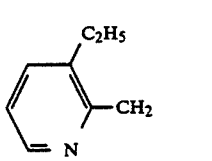 | H |  |
| (pyridine with CH$_3$, CH$_3$, CH$_3$, CH$_2$—) | —CH$_3$ | (Br, CH$_3$ phenyl) |
| (pyridine with CH$_3$, CH$_3$, CH$_3$, CH$_2$—) | —CH$_3$ | (Br, Cl phenyl) |
| (pyridine with C$_2$H$_5$, CH$_3$, CH$_2$—) | H | (phenyl H, H) |

TABLE 2-continued

| $R_a$ | $R_5$ | $R_6$ |
|---|---|---|
| 3-ethyl-2-pyridylmethyl | H | 2-bromo-6-methylphenyl |
| 3-ethyl-2-pyridylmethyl | H | 2,6-dimethylphenyl |
| 4,6-dimethyl-5-pyrimidinyl | —CH₃ | 2,6-dimethylphenyl |
| 4,6-dimethyl-5-pyrimidinyl | H | 2,6-dichlorophenyl |
| 4-pyridyl | H | 2-chloro-6-methylphenyl |
| 4-pyridyl | H | 2-chlorophenyl |
| 2-imidazolyl (NH) | H | 2-bromo-6-methylphenyl |
| 2-imidazolyl (NH) | H | 2-bromo-6-chlorophenyl |
| 2-imidazolyl (NH) | H | phenyl |
| 2-imidazolinyl (NH) | H | 2-bromo-6-methylphenyl |
| 2-imidazolinyl (NH) | H | 2,6-dimethylphenyl |
| 2-pyranyl | H | 2,6-dimethylphenyl |
| 2-pyranyl | H | 2,6-dichlorophenyl |
| 3-furyl | H | 2-chloro-6-methylphenyl |
| 3-furyl | H | 2-chlorophenyl |
| 3-thienyl | H | 2-bromo-6-methylphenyl |
| 3-thienyl | —CH₃ | 2-bromo-6-chlorophenyl |

TABLE 2-continued

| $R_a$ | $R_5$ | $R_6$ |
|---|---|---|
| N-methyl-dihydropyridinyl (CH3 on N) | —H | phenyl |
| N-methyl-dihydropyridinyl (CH3 on N) | —H | 4-bromo-3-methylphenyl (Br, CH3) |
| N-methoxy-dihydro (N—O, CH3) | —H | 2,4-dimethylphenyl (CH3, CH3) |
| 4,6-dimethylpyridin-2-yl (CH3, CH3) | H | 2,4-dimethylphenyl (CH3, CH3) |
| 4,6-dimethylpyridin-2-yl (CH3, CH3) | H | 2,6-dichlorophenyl (Cl, Cl) |
| 4,6-dimethylpyridin-2-yl (CH3, CH3) | H | 2-chloro-4-methylphenyl (Cl, CH3) |
| 4,6-dimethyl-dihydropyridinyl (CH3, CH3) | H | 2-chlorophenyl (Cl, H) |
| 4,6-dimethyl-dihydropyridinyl (CH3, CH3) | —CH3 | 2-bromo-4-methylphenyl (Br, CH3) |
| 3,5-dimethylpyridin-4-yl (CH3, CH3) | —CH3 | 2-bromo-4-chlorophenyl (Br, Cl) |
| 3-ethylpyridin-2-yl (C2H5) | H | phenyl (H, H) |
| 3-ethylpyridin-2-yl (C2H5) | H | 2-bromo-4-methylphenyl (Br, CH3) |
| 3-ethylpyridin-2-yl (C2H5) | H | 2,4-dimethylphenyl (CH3, CH3) |

Amidinoureas can be used in the practice of this invention in the form of a pharmaceutically acceptable salt. For example, they may be readily converted to their nontoxic acid addition salts by customary methods used in the art. Nontoxic salts of this invention can be formed from the base amidinourea and an acid which is pharmacologically acceptable in the intended dosages. Such salts include those prepared from inorganic acids, organic acids, higher fatty acids, high molecular weight acids, etc. Exemplary acids are hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

Prophylactic and therapeutic compositions containing amidinoureas are effective against coccidial infections and are useful for the treatment of humans and animals. Preferred compounds have a combination of desirable properties. For example, they combine specificity of action, moderate duration of host retention, and a high therapeutic index (therapeutic index is described as the ratio of the 50% suppressant dose to the 50% lethal dose). Standardized screening techniques for the identification of active anti-coccidial compositions have been used to evaluate amidinoureas within the scope of the present invention. See, the in vitro screening method described by McDougald and Galloway, in "Eimeria tenella: Anticoccidial Drug Activity in Cell Cultures," *Experimental Parasitology*, Vol. 34, No. 2, p. 189–196 (1973).

Following standard procedures for ascertaining anticoccidial activity, compounds of Formulae I and II have been administered to chickens at varying levels in their feed. The following test procedures are useful for ascertaining the in vivo anti-coccidial activity of the amidinoureas.

Test I

Determination of Anti-coccidial Activity

Hubbard broiler cockerels obtained from a commercial hatchery are maintained in disease-free rooms with uniform heat and lighting and fed unmedicated ration until they are 12 days old. Distribution to treatment groups is on a weight basis to achieve equal groups.

A culture of Eimeria recently isolated from a commercial poultry farm and containing mostly *E. tenella* is freshly propagated and assayed prior to use to assure pathogenicity.

Each of 8 treatments is replicated in 4 cages of 10 birds each. The drug is premixed in finely ground corn prior to mixing in a standard broiler starter ration. The treatments include groups of: uninfected unmedicated control chickens; infected, unmedicated control chickens; and infected birds treated with the test compound at 5, 15, 30, 60, 125 and 250 ppm. The replicates of each treatment are distributed so as to insure equal exposure to environmental variables.

Medication is started 2 days before infection. At 14 days old, the birds are infected using the pathogenic field isolate of *E. tenella*. The birds are observed daily and any untoward effects of the drug or pathological signs are recorded. The test is terminated 7 days post-inoculation. The birds are weighed and weight is calculated for days 0–7 post-inoculation. Feed consumption is measured. A necropsy is conducted and lesion scores for coccidiosis lesions are recorded.

Test 2

Spectrum of Anti-coccidial Activity

Broiler chicks from a commercial hatchery are assigned to treatments at 12 days of age. Medicated feeds and water are given ad libitum throughout. After 2 days on feed, chicks are infected with coccidia by oral inoculation. Birds are weighed at the start and at termination, and feed consumption is recorded.

The treatment of the birds is as follows:

| Treatment | Inoculum | Cages |
|---|---|---|
| Unmedicated | Uninoculated | 1, 2, 3 |
| Unmedicated | *E. acervulins* | 4, 5, 6 |
| Test compound, 60 ppm | " | 7, 8, 9 |
| Test compound, 30 ppm | " | 10, 11, 12 |
| Test compound, 20 ppm | " | 13, 14, 15 |
| Test compound, 10 ppm | " | 16, 17, 18 |

The test procedure is also conducted with coccidia species, *E. maxima, E. necatrix,* and *E. tenella.*

The following data is collected:
1. Daily observations for untoward drug effects.
2. Record deaths twice daily and autopsy dead birds.
3. Weigh birds at the start (for randomization) at infection, and 7 days postinoculation.
4. Weigh feed issued and returned, and calculate feed consumption.
5. Record lesion amounts of birds killed on 7 day postinoculation.

Test 3

Nature of Anti-coccidial Activity Coccidiocidal v. Coccidiostatic

Three groups of 5 broiler chicks from a commercial hatchery are assigned at 12 days of age to the bottom cages of a Petersime battery and given experimental rations. After two days on experimental rations, all birds are infected with *Eimeria tenella*. One group of birds is unmedicated throughout the 15 day period of the experiment. Medicated feeds of one group are replaced by unmedicated feed on day 7 post-inoculation. Feces are collected on days 4–15 and examined for coccidia oöcysts. Oöcysts counts are made by standard techniques. Birds are moved to clean upper cages on days 7, 9, 11 and 13 postinoculation, to prevent reinfection.

Additional tests for the development of drug resistance and the mechanism of anti-coccidial action are also conducted to ascertain the scope of anti-coccidial action of the compounds.

Tests show that amidinoureas in their free base form and in the form of their pharmaceutically acceptable salts are useful for both the prophylaxis and curative therapy of coccidiosis in poultry. The present invention can be used to treat single and multiple infections, that is, infections caused by a single species or by a combination of species.

Compounds defined above are readily absorbed into the blood stream from the stomach and intestines when taken orally, and therefore, the preferred method of treatment is to give the drug orally which is also the safest and most practical route of administration. Optional modes can be used where, for example, the human or animal is not eating or cannot swallow or has difficulty in swallowing. Other methods of administration which permit the drug to be absorbed in the gastrointestinal tract or which deliver a solution of the drug directly to the blood stream can be employed.

The method of administration may also vary depending on the purpose of administration. For example, use as a prophylaxis or preventive treatment, or as a pre-immunity suppressant, or as a treatment of infected animals can require different methods of treatment and dosage forms easily formulated by those skilled in the art.

The dosage regimens in carrying out this invention utilizing the amidinourea compositions for suppression of coccidiosis are those which insure maximum therapeutic response. The average effective daily dose is between about 0.1 to about 15 mg/kg of body weight with about 1 to about 10 mg/kg of body weight being preferred.

Compositions useful in the practice of the present invention can be prepared in forms suitable for administration by compounding an effective single dose amount of the compound with known ingredients generally employed in the preparation of therapeutic compositions of the type which are provided as tablets, hard or soft capsules, lozenges, pills, powders, granules, aqueous or oily suspensions, oil in water or water in oil emulsions, syrups and elixirs, and which can be taken orally.

The treatment of animals can be accomplished by incorporating an effective amount of the compound in the animal diet as a feed supplement or dissolved in the animals liquid intake. Amidinoureas for use in the practice of the present invention include compounds which are nontoxic to the animal host, including poultry, when administered to the animal in the animal's feed diet in concentrations of about 5 to about 500 ppm. Anti-coccidial non-toxic effects can be realized also for various of the amidinoureas when administered in the animal feed diet in concentrations of about 20 to about 250 ppm.

Compositions intended for oral use may be prepared according to methods known generally in the art. Such compositions may contain one or more agents selected from the group consisting of sweetening agents, flavoring agents, coloring agents, and preserving agents. In general, the composition will contain the active amidinourea ingredient in admixture with non-toxic pharmaceutically acceptable excipients. Exemplary excipients are: interdilutants such as calcium carbonate, sodium carbonate, lactose, calcium phosphate, and sodium phosphate; granulating or disintegrating agents, for example, maize, starch, and algenic acid; binding agents, for example, starch, gelatin, and acacia; and lubricating agents, for example, magnesium stearate, stearic acid, and talc. Tablets may be uncoated or they may be coated by known techniques to make them more effective, for example, to delay disintegration or absorption, or to make them more palatable, or for other reasons for which orally administered drugs have been previously provided in coated form.

Formulations for oral use may also be presented as hard gelatin capsules wherein the active ingredient is mixed with an inert solid diluent, for example, calcium carbonate, calcium phosphate and kaolin, or as soft gelatin capsules wherein the active ingredient is mixed with an oil medium, for example, arachis oil, liquid paraffin and olive oil.

Aqueous solutions containing the active anti-coccidial amidinourea comprise a further embodiment of compositions according to this invention. Excipients suitable for aqueous suspensions may be employed, if desired. Such excipients include: suspending agents, for example, sodium carboxymethyl-cellulose, methylcellulose, hydroxypropylmethylcellulose, sodium alginate, polyvinylpyrrolidine, gum tragacanth and gum acacia; and dispersing or wetting agents which may be a naturally occurring phosphatide, for example, lecithin, condensation products of an alkylene oxide with fatty acids, for example, polyoxyethylene stearate, condensation products of ethylene oxide with long-chain aliphatic alcohols, for example, heptadecaethylenoeoxy-cetanol, condensation products of ethylene oxide with partial esters derived from fatty acids and a hexitol, for example, polyoxyethylene sorbitol monoleate, and condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl-p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil, and coconut oil, or in a mineral oil, such as, liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing, suspending or wetting agent. Additional excipients, for example, sweetening, flavoring and coloring agents may also be present.

The compositions for use in the practice of this invention may also be in the form of oil-in-water emulsions. The oily phase may be vegetable oil, for example, olive oil, arachis oils, and mineral oil, for example, liquid paraffin or mixtures thereof. Suitable emulsifying agents may be naturally-occurring phosphatides, for example, soya bean licithin, and esters or partial esters derived from fatty acids and hexitol anhydrides, for example, sorbitan mono-oleate. The emulsions may also contain sweetening and flavoring agents.

Syrups and elixers may be formulated with sweetening agents, for example, glycerol, sorbitol and sucrose. Such formulations may also contain a demulcent, a preservative and flavoring and coloring agents.

The pharmaceutical compositions may be in the form of a sterile injectionable preparation, for example, as a sterile injectable aqueous suspension. This suspension may be formulated according to available art methods using those suitable dispersing or wetting agents and suspending agents which have been mentioned above or others. This sterile injectable preparation may also be a sterile injectable solution or suspension in a non-toxic parenterally acceptable diluent or solvent, for example, as an aqueous solution buffered to a pH of 4.0 to 7.0 and made isotonic with sodium chloride.

Further, the active amidinourea may be administered alone or in admixture with other amidinoureas or with other agents having the same, similar or different pharmacological properties.

Other suitable pharmaceutical carriers for human use are described in E. W. Martin et al., "Remington's Pharmaceutical Sc" 14th Ed., Mark Publishing Company, Easton, PA, 1965. Additionally, subcutaneous implants of anticoccidium compounds may be used. See, U.S. Pat. No. 4,159,322.

EXAMPLES

The following examples show veterinary and pharmaceutical compositions containing active amidinoureas for use in the practice of this invention and serve to illustrate the preparation thereof.

EXAMPLE 1

(A) 25 g of (2,6-dichlorophenylamidino)urea and
(B) 175 g of peanut oil
are intimately mixed with each other. Portions of 200 mg each of said mixture are filled into soft gelatin capsules thus containing 25 mg of the active phenylamidinourea compound. The capsules are suitable for administration to humans and small animals for the prophylactic or curative treatment of coccidial infections.

EXAMPLE 2

Ten thousand tablets for oral use, each containing 50 mg of 1-(2,6-dichlorophenylamidino)-3-n-propylurea are prepared from the following types and amounts of materials.

| Ingredient | Grams |
| --- | --- |
| 1-(2,6-dichlorophenylamidino)-3-n-propylurea | 500 |
| lactose U.S.P. | 350 |
| potato starch U.S.P. | 346 |

The mixture is moistened with an alcoholic solution of 20 g of stearic acid and granulated through a sieve and added to the following mixture.

| Ingredient | Grams |
| --- | --- |
| potato starch U.S.P. | 320 |
| talcum | 400 |
| magnesium stearate | 500 |
| lactose | 64 |

The mixture is thoroughly mixed and compressed into tablets. The tablets are especially useful for human use.

EXAMPLE 3

An elixir in which each 5 ml contains 50 mg of 1-(2,6-dimethylphenyl)-3-[(2-pyridylmethyl)amidino]urea hydrochloride is prepared by diluting 750 ml of invert sugar with 100 ml of water and adding to this 0.3 g of benzoic acid and 10 g of 1-(2,6-dimethylphenyl)-3-[2-(pyridylmethyl)amidino]urea hydrochloride. One hundred ml of alcohol (U.S.P. containing 0.2 g of flavors) are added and water is added to a total volume of 1 liter. The solution is thoroughly mixed, filtered, and bottled. The preparation is useful for administering to humans, small animals and avians for prophylactic treatment in combatting coccidial infections.

EXAMPLE 4

Capsules are prepared from
150 g of 1-(4-bromo-2-chloro-6-methylphenyl)-3-methylamidinourea hydrochloride,
3 g magnesium stearate,
2 g of finely divided silica sold under the trademark CAB-O-SIL by Godfrey L. Cabot, Inc., Boston, MA, and
234 g of lactose.
The ingredients are thoroughly mixed with each other and the mixture is filled in gelatin capsules. Each capsule contains 500 mg of the composition and thus 150 mg of 1-(4-bromo-2-chloro-6-methylphenyl)-3-methylamidinourea hydrochloride. The capsules can be administered to humans or small animals.

EXAMPLE 5

Tablets are prepared from
100 g of 1-(2-chloro-6-methylphenyl)-3-ethylamidinourea hydrochloride,
20 g of corn starch,
14 g of calcium carbonate, and
1 g of magnesium stearate.
The active compound and starch are thoroughly mixed, moistened with a 10 percent gelatin solution, and granulated by pressing through a No. 20 sieve. The granules are dried, thoroughly mixed with calcium carbonate and magnesium stearate, and compressed into tablets, each weighing about 125 mg and containing 100 mg. The tablets are suitable for administration to humans and small animals.

EXAMPLE 6

A composition is prepared from
75 g of 1-(2-chlorophenyl)-3-ethylamidinourea hydrochloride,
50 g of microcrystalline cellulose,
10 g of polyvinylpyrrolidine,
5 g of magnesium stearate, and
85 g of starch.
The active compound and cellulose are intimately mixed, moistened with a polyvinylpyrrolidine solution in water, and granulated by pressing through a No. 10 sieve. The dried granules are mixed with starch and magnesium stearate and are compressed to dragee cores, each weighing 225 mg. The cores are now provided with an elastic subcoat of an aqueous sugar solution containing 60 g of powdered acacia, 60 g of powdered gelatin, and 600 g of sugar per liter of solution. Thereafter a dusting powder mixture of 180 g of powdered sugar, 60 g of powdered starch, 1 g of powdered talc, and 1 g of powdered acacia is applied to the dragee cores. Coating with the gelatin subcoat and dusting are repeated about five times. The thus treated cores are sugar coated in the coating pan with a 60 percent sugar solution. Sugar coating is repeated until each dragee weighs about 400 mg. The preparation is suitable for administration to humans and small animals.

EXAMPLE 7

This example illustrates the utilization of a representative member of the compounds of the present invention as a coccidiostatic agent in an animal feed. In a manner similar to that described below, other compounds encompassed by the present invention may also be incorporated as active coccidiostatic agents into animal feeds.

A medicated poultry feed intended as a starter feed for broilers is prepared by blending about 0.005 percent by weight of 1-(2-bromo-6-methylphenyl)-3-n-propylamidinourea in a basic poultry ration containing:

| Ingredient | Amount |
| --- | --- |
| corn meal, No. 2 yellow, ground, g | 1123 |
| stabilized grease or vegetable oil, g | 60 |
| soybean oil meal (Low fiber content 50% protein), g | 480 |
| corn gluten meal, g | 50 |
| fish meal, antioxidant treated, 60% protein, g | 30 |
| fish solubles, dried basis, g | 10 |
| meat and bone scraps, 50% protein, g | 140 |
| corn distillers dried solubles, g | 50 |
| alfalfa meal, 17% protein 100,000 A/lb | 30 |
| salt iodized, g | 5 |
| manganese sulfate, feed grade, g | 0.75 |
| zinc carbonate or oxide, g | 0.25 |
| riboflavin, g | 3 |
| vitamin $B_{12}$, g | 6 |
| calcium pantotheante, g | 5 |
| niacin, g | 30 |
| stabilized vitamin A USP units | 6,000,000 |
| vitamin $D_3$, IC units | 650,000 |
| vitamin E acetate, IU | 5,000 |
| vitamin E (menadione sodium bisulfite), g | 2 |
| DL-methionine or hydroxy analog, lb | 1 |
| antioxidant (ethoxyquin or butylated hydroxy toluene), lb | 0.25 |

Similar feeds can be prepared containing one or more of other of the active amidinourea compounds.

EXAMPLE 8

Encapsulates of 1-(2,6-dimethylphenyl)-3-isopropyl amidinourea hydrochloride are prepared by the procedure of U.S. Pat. No. 3,773,919 as follows. Poly-L-lactide (10 g) and 1 g of 1-(2,6-dimethylphenyl)-3-isopropyl amidinourea hydrochloride are mixed and warmed to the melting point of the lactide. The mixture is cooled and ground into powder. Two grams of the powder injected subcutaneously by syringe into a feed-lot cattle and sheep would expectably reduce oöocysts counts and increase weight gain rate.

EXAMPLE 9

Encapsulates of 1-(2-bromo-6-methylphenyl)-3-(methylamidino)urea hydrochloride are prepared following the procedure of U.S. Pat. No. 3,523,906 as follows. Five g of the polycarbonate of 2,2-bis(4-hydroxyphenyl)propane are dissolved in 50 cc of methylene chloride to prepare a solution. One g of salimonycin is dispersed in this solution. The solution is emulsified to fine droplets in 150 ml of ethylene glycol and the methylene chloride gradually evaporated. The solid microcapsules are collected by centrifuge and rinsed with water. When subcutaneously implanted in feed-lot cattle and sheep, or cattle or sheep on pasture, there is obtained a reduction in fecal counts of coccidia oöocysts and improved weight gain rate.

As mentioned above, implants in the form of encapsulates release the amidinourea compound in an amount such that the blood contains 10–20-nanogram %. As shown in the examples, various types of encapsulates may be used, all of which may have varying rates of release of the compound, and, when taken with the variation in sizes of animals, it can be readily realized that varying sizes in implants, will be required depending on the situation. In general, however, the size of the implant will vary from about 0.5 to about 4 g and, if necessary, multiple dosage forms may be administered to large animals such as cattle. The amount of amidinourea in the implant may vary from about 5 to 95 wt%. Encapsulates may be inserted through a slit in the skin or in the case of microcapsules, administered by injection equipment.

Test results indicate that compounds falling within the scope of Formula IX below exhibit a good degree of activity:

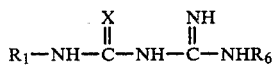

IX wherein X is oxygen or sulfur and wherein $R_1$ and $R_6$ are as defined in Formula I above. Representative compounds of Formula IX are exemplified below:

1-(2-chloro-6-methylphenyl)-3-[(2',2',2'-trifluoroethyl)amidino]urea;
1-(2,6-dimethylphenyl)-3-methylamidinourea;
1-(2,6-dimethylphenyl)-3-(3-methybutoxy)amidinourea;
1-(2,6-dimethylphenyl)-3-(n-propylamidino)urea;
1-(2,6-dimethylphenyl)-3-ethylamidinourea;
1-(n-propylamidino)-3-(2,4,6-trimethylphenyl)urea;
1-(4-trifluoromethylphenyl)-3-n-propylamidinourea;
1-(α-napthyl)-3-methylamidinourea;
1-(2,6-dimethylphenyl)-3-isobutylamidinourea;
1-(2-chloro-6-methylphenyl)-3-methylamidinothiourea;
1-(2-methylphenyl)-3-ethylamidinourea;
1-(2-trifluoroethylphenyl)-3-ethylamidinourea; and
1-[2-(5-chloropyridyl)]-3-methylamidinothiourea.

As is known, the literature includes reports that various amidinoureas are effective for treating certain diseases in animals, including man. For example, it has been reported that various amidinoureas are effective in treating diarrheal disorders in mammalian species. However, it has not heretofore been known that amidinoureas are effective in treating coccidiosis. As noted above, there are many other classes of compounds that have been reported for use as anti-coccidial agents. Typically, such anti-coccidial agents are administered to animals in feed supplements along with other materials including, for example, nutrients and other medicaments.

In the practice of the present invention, the source of effective anti-coccidial dose can be solely an amidinourea or mixture of amidinoureas. According to conventional practices, the anti-coccidial amidinourea can be administered to animals in a feed supplement along with other materials, for example, nutrients and other medicaments.

Alternatively, the anti-coccidial amidinourea can be used in combination, for example, in admixture, with other anti-coccidial agents. Thus, the present invention can be practiced by including in the animal's diet an effective anti-coccidial dose of a combination of individually ineffective coccidiostatic doses of an amidinourea and other anti-coccidial agent.

In view of the above, it should also be appreciated that the present invention encompasses within its scope the formulation of an animal feed supplement containing other materials in combination with an amidinourea as the sole effective anti-coccidial agent, or a mixture of individually ineffective coccidiostatic doses of an amidinourea and other anti-coccidial agent, as an effective anti-coccidial medication.

In summary, it can be stated that the present invention provides an important advance in the art characterized by a number of advantages which flow from its use. Amidinoureas within the scope of the present invention exhibit relatively high activity when used in doses well below their toxic doses. Thus, the use of such amidinoureas do not require the strict control of the type required by currently used anticoccidial compounds which are highly toxic. In addition, amidinoureas within the scope of the present invention do not give rise to the animal tissue residue problem associated with other anti-coccidial agents, the use of which must be terminated weeks prior to the animal's slaughter. Amidinoureas within the scope of the present invention can be continuously used in the animal's diet up to the time of slaughter of the animal or a few days prior to slaughter.

We claim:

1. A method for the prophylactic or curative treatment of coccidiosis in a population of animals including infected animals comprising administering to the animal population an effective amount of an anti-coccidial compound according to either Formula I or Formula II

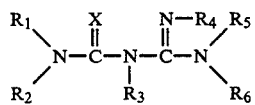

Formula I

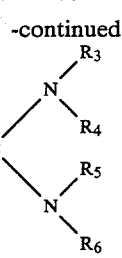

Formula II wherein:

X is oxygen or sulfur;

$R_1$, $R_2$, $R_3$, $R_4$, $R_5$ and $R_6$ are hydrogen, alkyl, cycloalkyl, cycloalkenyl, bicycloalkyl, alkenyl, alkynyl, alkoxy, hydroxy, haloalkyl, haloalkenyl, hydroxyalkyl, alkoxyalkyl, cyanoalkyl, aminoalkyl, mono- or di-alkyl aminoalkyl, carbamoylylalkyl, mono- or di-alkyl carbamoyl lower alkyl, alkoxy carbamoylalkyl, aralkoxy carbamoylalkyl, acyl, alkylsulfonyl, aralkylsulfonyl, aryl, aralkyl, heterocyclyl, substituted heterocyclyl, heterocyclylalkyl or substituted heterocyclylalkyl;

$R_1$ and $R_2$ together with the nitrogen to which they are attached may form a mono- or bicyclic 5 to 10 member heterocycle containing 0 to 4 additional heteroatoms of oxygen, nitrogen or sulfur;

$R_5$ and $R_6$ together with the nitrogen to which they are attached may form a mono- or bicyclic 5 to 10 member heterocycle, containing 0 to 4 additional heteroatoms of oxygen, nitrogen or sulfur;

$R_4$ and $R_5$ together with the nitrogens to which they are attached may form a mono- or bicyclic 5 to 10 member heterocycle, containing 0 to 4 additional heteroatoms of oxygen, nitrogen or sulfur;

provided that at least one of $R_1$, $R_2$, $R_3$, $R_4$, $R_5$ and $R_6$ is other than hydrogen;

and wherein:

"heterocyclylalkyl" means an alkyl group substituted by a heterocyclyl group;

"heterocyclyl" and "heterocycle" means a 3, 5, 6, 7, 8, 9 or 10 member ring having 1 to 5 hetero atoms which may be nitrogen, oxygen or sulfur, including morpholinyl, thiazolidinyl, piperazinyl, thiamorpholinyl, trimethylenetriaminyl, ethyleneiminyl, 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole; and "substituted heterocyclyl" and "substituted heterocycle" means a heterocyclyl or heterocycle which is mono-, di-, tri- or tetrasubstited by lower alkyl, lower alkenyl, lower alkynyl, aryl, aralkyl, halo, nitro, cyano, sulfonyl, hydroxyl, carboxyl, lower alkanoyl, lower carboalkoxy, loweralkoxy, aryl-loweralkoxy, haloloweralkoxy, amido, amino, loweralkylamino, dialkylamino, loweralkoxyamino, and aralkylamino;

and, pharmaceutically acceptable salts thereof.

2. A method according to claim 1 wherein at least one of $R_1$ and $R_5$ is aryl, aralkyl, heterocyclyl, heterocyclylalkyl, substituted heterocyclyl or substituted heterocyclylalkyl.

3. A method according to claim 2 wherein: at least one of $R_1$ and $R_5$ is aryl or aralkyl.

4. A method according to claim 2 wherein: at least one of $R_1$ and $R_5$ is heterocyclyl, heterocyclylalkyl, substituted heterocyclyl or substituted heterocyclylalkyl.

5. A method according to claim 3 wherein at least one of $R_1$ and $R_5$ is a group of the formula

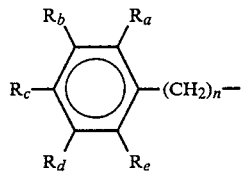

wherein:

n is 0, 1, 2 or 3;

$R_a$, $R_b$, $R_c$, $R_d$ and $R_e$ are selected from the group including hydrogen, halo, alkyl, alkenyl, cycloalkenyl, cycloalkyl, alkoxy, hydroxy, cyano, amino, acyl, nitro, acyloxy, haloalkyl, alkoxyalkyl, aminoalkyl, arylalkoxy, haloalkoxy, alkylsulfonyl and acylamino.

6. A method according to claim 2 wherein at least one of $R_1$ and $R_5$ is a group of the formula

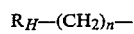

$R_H$—$(CH_2)_n$— and wherein: n is 0, 1, 2 or 3; and $R_H$ is a heterocycle selected from the group consisting of 1-pyrrole, 2-pyrrole, 3-pyrrole, 2-furan, 3-furan, 2-thiophene, 3-thiophene, 2-tetrahydrothiophene, 3-tetrahydrothiophene, 1-imidazole, 2-imidazole, 4-imidazole, 5-imidazole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine, 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole; where said heterocycle may be mono-, di-, tri- or tetra-substituted by ring substituents selected from the group consisting of hydrogen, lower alkyl, lower alkenyl, aryl, lower alkynyl, aralkyl, halo, nitro, cyano, sulfonyl, hydroxyl, carboxyl, lower alkanoyl, lower alkoxy, aryl lower alkoxy, halo lower alkoxy, amido, amino, lower alkylacyloxy, alkylamino, lower alkoxyamino, and aralkoxyamino.

7. A method according to claim 6 wherein $R_1$ is a group of the formula

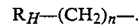

$R_H$—$(CH_2)_n$—.

8. A method according to claim 6 wherein $R_5$ is a group of the formula $R_H$—$(CH_2)_n$—.

9. A method according to claim 5 wherein at least one of $R_a$ or $R_e$ is other than hydrogen.

10. A method according to claim 1 wherein the anticoccidial compound is of the formula

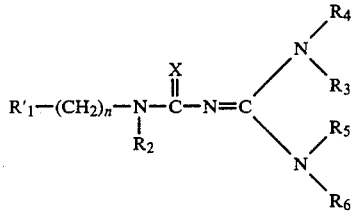

wherein:
X is oxygen or sulfur;
n is 0, 1, 2 or 3;
$R'_1$ is phenyl, substituted phenyl, heterocyclyl or heterocyclyl having one or more of the ring hydrogens replaced by lower alkyl, lower alkoxy, halo, halo lower alkyl, amino, acylamino, acyloxy, aryl lower alkoxy, halo lower alkoxy, nitro, hydroxy, cyano, carboxyl or lower alkyl sulfonyl;
and $R_2$, $R_3$, $R_4$, $R_5$ and $R_6$ are hydrogen, lower alkyl, lower alkoxy, lower alkenyl, cycloloweralkenyl, hydroxy, cycloloweralkyl, aryl, arloweralkyl, heterocyclyl, heterocyclyl lower alkyl, lower alkynyl, halo alkyl, hydroxy lower alkyl, lower alkoxy lower alkyl, cyano lower alkyl, amino lower alkyl, mono- or di-lower alkyl amino lower alkyl, carbamoyl lower alkyl, mono- or di-alkyl carbamoyl lower alkyl, lower alkoxy carbamoyl lower alkyl, aralkoxy carbamoyl lower alkyl, lower alkylacyl, alkyl sulfonyl or aralkyl sulfonyl; or
$R_5$ together with $R_6$ and the nitrogen to which $R_5$ and $R_6$ are attached or $R_5$ together with $R_3$ and the nitrogens to which they are attached may form a 5, 6, 7 or 8 membered heterocyclic ring which may include 0 to 2 additional hetero atoms which may be either oxygen, nitrogen or sulfur;
and pharmaceutically acceptable salts thereof.

11. A method according to claim 1 wherein the anticoccidial compound is of the formula

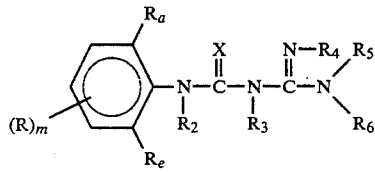

wherein:
X is oxygen or sulfur;
m is 0, 1, 2 or 3;
R, $R_a$, and $R_e$ are hydrogen, lower alkyl, halo, cyano, lower alkoxy, nitro, amino or halo lower alkyl;
$R_2$, $R_3$, $R_4$ and $R_5$ are hydrogen, lower alkyl, lower alkoxy, or halo lower alkyl;
$R_6$ is lower alkyl, lower alkoxy, halo lower alkyl, heterocyclyl or heterocyclyloweralkyl;
provided that at least one of $R_a$ or $R_e$ is other than hydrogen;
and pharmaceutically acceptable salts thereof.

12. A method according to claim 11 wherein at least one of $R_a$ and $R_e$ is lower alkyl, halo or halo loweralkyl.

13. A method according to claim 1 wherein the anticoccidial compound is of the formula

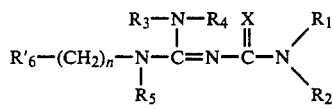

wherein:
X is oxygen or sulfur;
n is 0, 1, 2 or 3;
$R'_6$ is phenyl, substituted phenyl, heterocyclyl or heterocyclyl having one or more of the ring hydrogens replaced by lower alkyl, lower alkoxy, halo, halo lower alkyl, amino, acylamino, acyloxy, aryl lower alkoxy, halo lower alkoxy, nitro, hydroxy, cyano, carboxyl or lower alkyl sulfonyl;
and $R_1$, $R_2$, $R_3$, $R_4$ and $R_5$ are hydrogen, lower alkyl, lower alkoxy, lower alkenyl, cyclo lower alkenyl, hydroxy, cycloloweralkyl, aryl, arloweralkyl, heterocyclyl, heterocyclyl lower alkyl, lower alkynyl, halo alkyl, hydroxy lower alkyl, lower alkoxy lower alkyl, cyano lower alkyl, amino lower alkyl, mono- or di-lower alkyl amino lower alkyl, carbamoyl lower alkyl, mono- or di-alkyl carbamoyl lower alkyl, lower alkoxy carbamoyl lower alkyl, aralkoxy carbamoyl lower alkyl, lower alkylacyl, alkyl sulfonyl or aralkyl sulfonyl; or, $R_1$ together with $R_2$ and the nitrogen to which they are attached or $R_3$ together with $R_4$ and the nitrogen to which they are attached or $R_3$ together with $R_5$ and the nitrogen atoms to which they are attached, may form a 5, 6, 7 or 8 membered heterocyclic ring which may include 0 to 2 additional hetero atoms which may be either oxygen, nitrogen or sulfur;
and pharmaceutically acceptable salts thereof.

14. A method according to claim 1 wherein the anticoccidial compound is of the formula

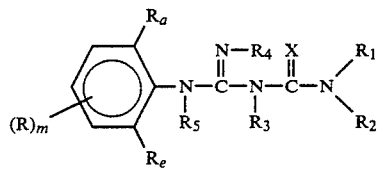

wherein:
X is oxygen or sulfur;
m is 0, 1, 2 or 3;
R, $R_a$ and $R_e$ are hydrogen, lower alkyl, halo, cyano, lower alkoxy, nitro, amino or halo lower alkyl;
$R_1$, $R_3$, $R_4$ and $R_5$ are hydrogen, lower alkyl, lower alkoxy, or halo lower alkyl;
$R_2$ is lower alkyl, lower alkoxy, halo lower alkyl, heterocyclyl or heterocyclyl lower alkyl;
provided that at least one of $R_a$ or $R_e$ is other than hydrogen;
and pharmaceutically acceptable salts thereof.

15. A method according to claim 14 wherein at least one of $R_a$ and $R_e$ is lower alkyl.

16. A method according to claim 1 wherein the anticoccidial compound is 1-(2-methyl-6-chlorophenyl)-3-n-propylamidinourea; and pharmaceutically acceptable salts thereof.

17. A method according to claim 1 wherein the anti-coccidial compound is 1-(2-chlorophenyl)-3-ethylamidinourea; and pharmaceutically acceptable salts thereof.

18. A method according to claim 1 wherein the anti-coccidial compound is 1-(2,6-dimethylphenyl)-3-[(2-pyridylmethyl)amidino]urea; and pharmaceutically acceptable salts thereof.

19. A method according to claim 1 wherein the anti-coccidial compound is 1-(2-chloro-6-methylphenyl)-3-[(2′,2′,2′-trifluoroethyl)amidino]urea; and pharmaceutically acceptable salts thereof.

20. A method according to claim 1 wherein the anti-coccidial compound is 1-(2,6-dimethylphenyl)-3-methylamidinourea; and pharmaceutically acceptable salts thereof.

21. A method according to claim 1 wherein the anti-coccidial compound is 1-(2-chloro-6-methylphenyl)-3-ethylamidinourea; and pharmaceutically acceptable salts thereof.

22. A method according to claim 1 wherein the anti-coccidial compound is 1-(2,6-dimethylphenyl)-3-[3-methylbutoxy)amidino]urea; and pharmaceutically acceptable salts thereof.

23. A method according to claim 1 wherein the anti-coccidial compound is 1-(2,6-dimethylphenyl)-3-ethylamidinourea; and pharmaceutically acceptable salts thereof.

24. A method according to claim 1 wherein the anti-coccidial compound is 1-(2,6-dimethylphenyl)-3-n-propylamidinourea; and pharmaceutically acceptable salts thereof.

25. A method according to claim 1 wherein the anti-coccidial compound is 1-(2,6-dimethylphenyl)-3-isopropylamidinourea; and pharmaceutically acceptable salts thereof.

26. A method according to claim 1 wherein the anti-coccidial compound is 1-(n-propylamidino)-3-(2,4,6 trimethylphenyl)urea; and pharmaceutically acceptable salts thereof.

27. A method according to claim 1 wherein the anti-coccidial compound is 1-(2-chloro-6-methylphenyl)-3-n-propylamidinourea; and pharmaceutically acceptable salts thereof.

28. A method according to claim 1 wherein the anti-coccidial compound is 1-(4-trifluoromethylphenyl)-3-n-propylamidinourea; and pharmaceutically acceptable salts thereof.

29. A method according to claim 1 wherein the anti-coccidial compound is 1-(α-napthyl)-3-methylamidinourea; and pharmaceutically acceptable salts thereof.

30. A method according to claim 1 wherein the anti-coccidial compound is 1-(2-,6-dimethylphenyl)-3-isobutylamidinourea; and pharmaceutically acceptable salts thereof.

31. A method according to claim 1 wherein the anti-coccidial compound is 1-(2-chloro-6-methylphenyl)-3-methylamidinothiourea; and pharmaceutically acceptable salts thereof.

32. A method according to claim 1 wherein the anti-coccidial compound is 1-(2-methylphenyl)-3-ethylamidinourea; and pharmaceutically acceptable salts thereof.

33. A method according to claim 1 wherein the anti-coccidial compound is 1-(2-trifluoroethylphenyl)-3-ethylamidinourea; and pharmaceutically acceptable salts thereof.

34. A method according to claim 1 wherein the anti-coccidial compound is 1-[2-(5-chloropyridyl)]-3-methylamidinothiourea; and pharmaceutically acceptable salts thereof.

35. A method according to any one of claims 1 to 34 wherein the animal treated with said anti-coccidial compound is a member of the avian species.

36. A method according to claim 35 wherein the avian species treated is poultry.

37. A method according to any one of claims 1 to 34 wherein said anti-coccidial compound is incorporated into a feed or liquid composition and fed to said animal on a daily basis.

38. A method according to claim 37 wherein said anti-coccidial compound is included in the daily diet of said animal in an amount between about 5 to about 500 ppm.

39. A method according to claim 1 wherein said anti-coccidial compound is of the formula

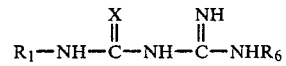

wherein X is oxygen or sulfur and wherein $R_1$ and $R_6$ are as defined in claim 2.

40. A method according to claim 39 wherein the animal treated with said anti-coccidial compound is a member of the avian species.

41. A method according to claim 40 wherein the avian species is poultry.

* * * * *